United States Patent
Shinde et al.

(10) Patent No.: US 11,259,527 B2
(45) Date of Patent: Mar. 1, 2022

(54) HAEMATOCOCCUS BASED COMPOSITIONS FOR PLANTS AND METHODS OF APPLICATION

(71) Applicant: HELIAE DEVELOPMENT LLC, Gilbert, AZ (US)

(72) Inventors: Sandip Shinde, Gilbert, AZ (US); Stephen Ventre, Mesa, AZ (US); Nicholas Donowitz, Shelbourne, VT (US); Michael Clint Rohlfsen, Edina, MN (US); Laura Carney, Chandler, AZ (US)

(73) Assignee: HELIAE DEVELOPMENT, LLC, Gilbert, AZ (US)

( * ) Notice: Subject to any disclaimer, the term of this patent is extended or adjusted under 35 U.S.C. 154(b) by 630 days.

(21) Appl. No.: 15/749,605

(22) PCT Filed: Aug. 17, 2016

(86) PCT No.: PCT/US2016/047271
§ 371 (c)(1),
(2) Date: Feb. 1, 2018

(87) PCT Pub. No.: WO2017/031160
PCT Pub. Date: Feb. 23, 2017

(65) Prior Publication Data
US 2018/0223246 A1  Aug. 9, 2018

Related U.S. Application Data

(60) Provisional application No. 62/206,138, filed on Aug. 17, 2015.

(51) Int. Cl.
A01N 65/03 (2009.01)
C05F 7/00 (2006.01)
(Continued)

(52) U.S. Cl.
CPC .............. *A01N 65/03* (2013.01); *C05F 7/00* (2013.01); *C05F 11/04* (2013.01); *C05F 11/08* (2013.01);
(Continued)

(58) Field of Classification Search
CPC .. C05F 11/00; C05F 11/10; C05F 7/00; C05F 11/04; C05F 11/08; C12N 1/12; A01N 63/10; C05G 5/30
(Continued)

(56) References Cited

U.S. PATENT DOCUMENTS 9,386,774 B2 * 7/2016 Shinde .................... C12N 1/12
2009/0188290 A1 7/2009 Marler
(Continued)

FOREIGN PATENT DOCUMENTS

CN 104387171 A 3/2015
JP 2010043032 11/2013
(Continued)

OTHER PUBLICATIONS

Michalak et al, "Algal Extracts: Technology and Advances," Engineering in Life Sciences, Nov. 1, 2014, vol. 14, pp. 581-591, entire document.

*Primary Examiner* — Melissa S Swain
(74) *Attorney, Agent, or Firm* — Hellae Development, LLC; Adam Lunceford; Veronica Adele R. Cao

(57) ABSTRACT

Methods of improving characteristics of plants and soil by administering an effective amount of a extracted *Haematococcus* based composition in low concentration applications are disclosed.

16 Claims, 1 Drawing Sheet

(51) Int. Cl.
 *C05F 11/08* (2006.01)
 *C05G 5/30* (2020.01)
 *C05F 11/04* (2018.01)
 *C12N 1/12* (2006.01)

(52) U.S. Cl.
 CPC ............... *C05G 5/30* (2020.02); *C12N 1/12* (2013.01); *Y02A 40/20* (2018.01)

(58) Field of Classification Search
 USPC .......................................................... 71/23
 See application file for complete search history.

(56) References Cited

U.S. PATENT DOCUMENTS

| | | | |
|---|---|---|---|
| 2012/0094831 A1* | 4/2012 | Bartley, Jr. | ............ A01N 65/00 |
| | | | 504/101 |
| 2013/0167432 A1 | 7/2013 | Kale | |
| 2013/0205850 A1 | 8/2013 | Ganuza | |
| 2014/0223981 A1 | 8/2014 | Hatcher | |
| 2016/0165896 A1* | 6/2016 | Shinde | ................... A01N 65/03 |
| | | | 504/117 |

FOREIGN PATENT DOCUMENTS

| | | | | |
|---|---|---|---|---|
| WO | 2007062274 | | 5/2007 | |
| WO | WO-2014167583 A1 * | | 10/2014 | ............. A01N 65/00 |
| WO | 2016100550 | | 6/2016 | |

* cited by examiner

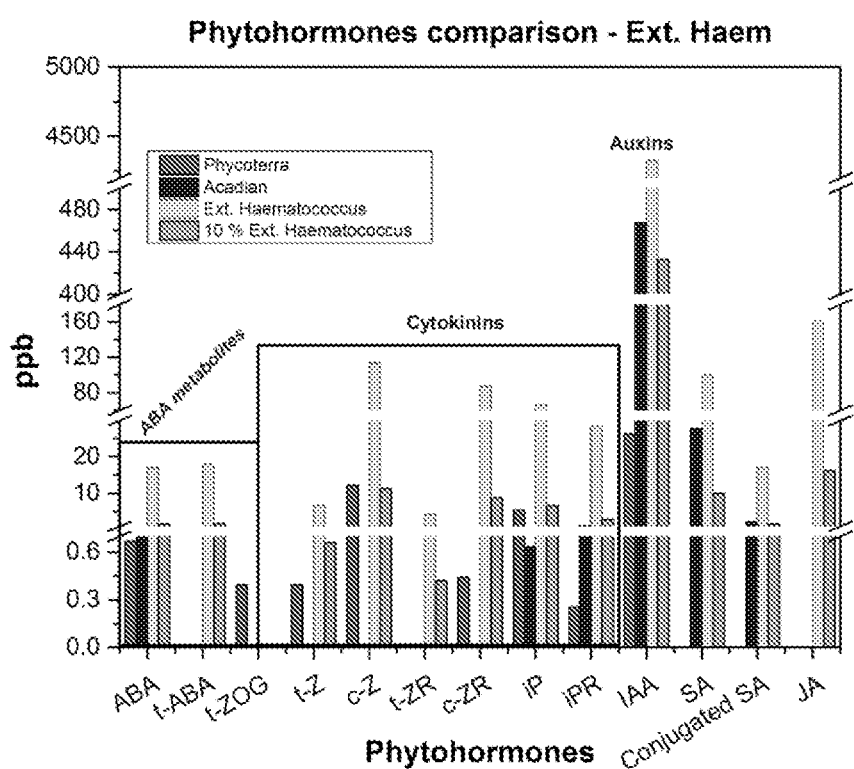

HAEMATOCOCCUS BASED COMPOSITIONS FOR PLANTS AND METHODS OF APPLICATION

CROSS REFERENCE TO RELATED APPLICATIONS

The present application is a U.S. National Stage entry under 35 U.S.C. § 371 of International Application No. PCT/US2016/47271, filed on Aug. 17, 2016, designating the United States of America and published in English on Feb. 23, 2017 which in turn claims priority to U.S. Provisional Application No. 62/206,138, filed Aug. 17, 2015, entitled Haematococcus Based Compositions for Plants and Methods of Application. The entire contents of all of the foregoing are hereby incorporated by reference herein.

BACKGROUND

Seed emergence occurs as an immature plant breaks out of its seed coat, typically followed by the rising of a stem out of the soil. The first leaves that appear on many seedlings are the so-called seed leaves, or cotyledons, which often bear little resemblance to the later leaves. Shortly after the first true leaves, which are more or less typical of the plant, appear, the cotyledons will drop off. Germination of seeds is a complex physiological process triggered by imbibition of water after possible dormancy mechanisms have been released by appropriate triggers. Under favorable conditions rapid expansion growth of the embryo culminates in rupture of the covering layers and emergence of the radicle. A number of agents have been proposed as modulators of seed emergence. Temperature and moisture modulation are common methods of affecting seed emergence. Addition of nutrients to the soil has also been proposed to promote emergence of seeds of certain plants.

Additionally, whether at a commercial or home garden scale, growers are constantly striving to optimize the yield and quality of a crop to ensure a high return on the investment made in every growth season. As the population increases and the demand for raw plant materials goes up for the food and renewable technologies markets, the importance of efficient agricultural production intensifies. The influence of the environment on a plant's health and production has resulted in a need for strategies during the growth season which allow the plants to compensate for the influence of the environment and maximize production. Addition of nutrients to the soil or application to the foliage has been proposed to promote yield and quality in certain plants. The effectiveness may be attributable to the ingredients or the method of preparing the product. Increasing the effectiveness of a product may reduce the amount of the product needed and increase efficiency of the agricultural process.

SUMMARY

Compositions and methods are described herein increasing the emergence and yield of plants. The compositions can include cells from the genus Haematococcus in various states, such as but not limited to, whole cells, lysed cells, dried cells, and cells that have been subjected to an oil extraction process. The composition can include Haematococcus as the primary or sole active ingredient, or in combination with other active ingredients such as, but not limited to, extracts from macroalgae, extracts from microalgae, non-Haematococcus microalgae, and whole microalgae cultured phototrophically, mixotrophically, or heterotrophically. The compositions can be in the form of a liquid or dry form (powder, or the like). The compositions can be stabilized through the addition of stabilizers suitable for plants, pasteurization, and combinations thereof. The methods can include applying the compositions to plants or seeds in a variety of methods, such as but not limited to, soil application, foliar application, seed treatments, and/or hydroponic application. The methods can include single or multiple applications of the compositions, and may also comprise low concentrations of Haematococcus cells.

For example, some embodiments of the invention relate to a method for enhancing emergence of a plant from seed. In one non-limiting embodiment, the method can include administering a liquid composition that includes Haematococcus cells in which the cells consist essentially of cells that have been subjected to drying, mechanical lysing, and extraction processes. The liquid composition can be administered in a concentration in the range of 0.003-0.080% solids by weight to a planted seed in an amount effective to enhance emergence of seeds in a population of such seeds compared to seeds in a substantially identical population of untreated seeds.

In some embodiments, the administration can include contacting the soil in the immediate vicinity of the planted seed with an effective amount of the liquid composition. In some embodiments, the liquid composition can include 0.004-0.080% solids by weight of Haematococcus cells. In some embodiments, the liquid composition can be administered at a rate in the range of 50-150 gallons per acre.

In some embodiments, the liquid composition can be pasteurized. In some embodiments, the liquid composition can further include stabilizing means suitable for plants. In some embodiments, the liquid composition can further include whole Chlorella cells cultured in mixotrophic conditions. In some embodiments, the Chlorella cells can be cultured in non-axenic mixotrophic conditions. In some embodiments, the liquid composition can further comprise a liquid extract from Kappaphycus.

In some embodiments, the number plants emerged from the soil can be increased by at least 30% compared to a substantially identical population of untreated seeds of plants.

Some embodiments of the invention relate to a method of enhancing emergence of a plant from seed. The method can include: (a) providing a liquid composition including Haematococcus cells in which the cells consist essentially of cells that have been subjected to drying, mechanical lysing, and extraction processes, in a concentration in the range of 5-30% solids by weight; (b) diluting the liquid composition with water to a concentration in the range of 0.003-0.080% solids by weight of Haematococcus cells; and (c) administering the liquid composition to a planted seed in an amount effective to enhance emergence of seeds in a population of such seeds compared to seeds in a substantially identical population of untreated seeds. The administration can include contacting the soil in the immediate vicinity of the planted seed with an effective amount of the liquid composition.

In some embodiments, the administration can include contacting soil in the immediate vicinity of the plants with an effective amount of the liquid composition. In some embodiments, the liquid composition can include a concentration in the range of 0.004-0.080% solids by weight of Haematococcus cells. In some embodiments, the liquid composition can be pasteurized. In some embodiments, the liquid composition can further include stabilizing means suitable for plants. In some embodiments, the liquid composition can further include whole *Chlorella* cells cultured in mixotrophic conditions. In some embodiments, the *Chlorella* cells can be cultured in non-axenic mixotrophic conditions. In some embodiments, the liquid composition can further comprise a liquid extract from *Kappaphycus*.

Some embodiments of the invention relate to a method for enhancing yield of a plant. The method can include administering a liquid composition comprising *Haematococcus* cells in which the cells consist essentially of cells that have been subjected to drying, mechanical lysing, and extraction processes, in a concentration in the range of 0.001-0.400% solids by weight to a plant in an amount effective to increase utilization in a population of such plants compared to a substantially identical population of untreated plants.

In some embodiments, the administration can include contacting foliage of the plants with an effective amount of the liquid composition where, in some embodiments, the liquid composition includes a concentration in the range of 0.003-0.080% solids by weight of the *Haematococcus* cells and/or the composition can be administered at a rate in the range of 10-50 gallons/acre. In some embodiments, the liquid compositions can be administered by spraying. In some embodiments, the liquid composition can be administered every 3-28 days or every 4-10 days. In some embodiments, the liquid composition can be first administered 5-14 days after the plant emerges from the soil.

In some embodiments, the administration can comprise contacting soil in the immediate vicinity of the plants with an effective amount of the liquid composition, where in some the liquid composition can include a concentration in the range of 0.003-0.055% or 0.040-0.360% solids by weight of *Haematococcus* cells and/or the liquid composition can be administered at a rate in the range of 50-150 gallons per acre. In some embodiments, the liquid composition can be administered to the soil by a low volume irrigation system and/or a soil drench application.

In some embodiments, the liquid composition can further include stabilizing means suitable for plants. In some embodiments, the liquid composition can further include *Chlorella* cells cultured in mixotrophic conditions.

In some embodiments, the methods can further include increasing marketable plant weight, marketable plant yield, and/or marketable fruit weight. In some embodiments, the utilization can be increased by at least 80% compared to a substantially identical population of untreated plants. In some embodiments, the marketable plant weight can be increased by at least 125% compared to a substantially identical population of untreated plants. In some embodiments, the marketable plant yield can be increased by at least 100% compared to a substantially identical population of untreated plants. In some embodiments, the marketable fruit weight can be increased by at least 50% compared to a substantially identical population of untreated plants.

In some embodiments, the liquid composition can further include a liquid extract from *Kappaphycus*. In some embodiments, the liquid composition is pasteurized.

Some embodiments relate to a method of enhancing yield of a plant. In one non-limiting example, the method can include (a) providing a liquid composition including *Haematococcus* cells in which the cells consist essentially of cells that have been subjected to drying, mechanical lysing, and extraction processes, in a concentration in the range of 5-30% solids by weight; (b) diluting the liquid composition with water to a concentration in the range of 0.001-0.400% solids by weight of *Haematococcus* cells; and (c) administering the liquid composition to a plant in an amount effective to increase plant yield in a population of such plants compared to a substantially identical population of untreated plants.

In some embodiments, the liquid composition can be administered to soil in the immediate vicinity of the plants and/or foliage of the plants. In some embodiments, the liquid composition is administered every 3-28 days. In some embodiments, the liquid composition can be pasteurized. In some embodiments, the liquid composition can further comprise *Chlorella* cells cultured in mixotrophic conditions. In some embodiments, the *Chlorella* cells can be cultured in non-axenic mixotrophic conditions. In some embodiments, the liquid composition can further include a liquid extract from *Kappaphycus*.

Some embodiments of the invention relate to a composition including *Haematococcus* cells in which the cells consist essentially of cells that have been subjected to drying, mechanical lysing, and extraction processes, in a concentration in the range of 0.003-0.080% solids by weight, and water. Some embodiments of the invention relate to a composition including *Haematococcus* cells in which the cells consist essentially of cells that have been subjected to drying, mechanical lysing, and extraction processes, in a concentration in the range of 5-30% solids by weight, and water. The composition can further include whole *Chlorella* cells cultured in mixotrophic conditions. The composition can further include a liquid extract from *Kappaphycus*. The composition can be pasteurized.

Some embodiments relate to a method of plant enhancement. The method can include administering to a plant, seedling, or seed a composition treatment comprising 0.1-20% by volume of *Haematococcus* cells in which the cells consist essentially of cells that have been subjected to drying, mechanical lysing, and extraction processes to enhance at least one plant characteristic.

In some embodiments, the concentration of *Haematococcus* cells is 1-5% by volume. In some embodiments, the *Haematococcus* cells can be dried by freeze drying, spray drying, drum drying, crossflow air drying, solar drying, thin film convection oven drying, vacuum shelf drying, pulse combustion drying, flash drying, furnace drying, belt conveyor drying, and/or refractance window drying.

In some embodiments, the administrating can be coating a seed with the composition prior to planting; administering an effective amount to a solid growth medium prior to or after the planting of a seed, seedling, or plant; and/or mixing an effective amount of the composition in a suitable solid growth medium prior to planting a seed, seedling, or plant. In some embodiments, the solid growth medium can include soil, potting mix, compost, and/or inert hydroponic material.

In some embodiments, the plant characteristic can be seed germination rate, seed germination time, seedling emergence, seedling emergence time, seedling size, plant fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and/or sun burn.

Some embodiments relate to a composition including *Haematococcus* cells in which the cells consist essentially of cells that have been subjected to drying, mechanical lysing, and extraction processes, in a concentration in the range of 0.1-20% solids by volume, and a solid growth medium. In some embodiments, the concentration of *Haematococcus* cells can be 1-5% by volume. In some embodiments, the solid growth medium can include soil, potting mix, compost, and/or inert hydroponic material.

Some embodiments of the invention relate to a method of preparing a composition. The method can include (a) drying *Haematococcus* cells to a moisture content of 1-8% on a wet basis; (b) mechanically lysing the *Haematococcus* cells; (c) extracting oil from the dried and lysed *Haematococcus* cells to form an extracted biomass; and (d) mixing the extracted biomass with a medium.

In some embodiments, the extracted biomass can include 0.1-20% or 1-5% by volume of the composition. In some embodiments, the extracted biomass can include 0.003-0.080% or 5-30% by weight of the composition. In some embodiments, the medium can be water. In some embodiments, the medium can include soil, potting mix, compost, and/or inert hydroponic material. In some embodiments, the method can include pasteurizing the composition. In some embodiments, the *Haematococcus* cells can be dried by freeze drying, spray drying, drum drying, crossflow air drying, solar drying, thin film convection oven drying, vacuum shelf drying, pulse combustion drying, flash drying, furnace drying, belt conveyor drying, and/or refractance window drying. In some embodiments, the oil from the dried and lysed *Haematococcus* cells can be extracted by a supercritical carbon dioxide process.

Some embodiments of the invention relate to a method of plant enhancement including administering to a plant, seedling, or seed a composition treatment at a rate of 50-500 grams of *Haematococcus* cells per acre, in which the cells consist essentially of cells that have been subjected to drying, mechanical lysing, and extraction processes to enhance at least one plant characteristic. In some embodiments, the administrating can be in-furrow application during planting, and broadcast application.

DESCRIPTION OF THE FIGURES

FIG. 1 shows a graph of the phytohormone content in some microalgae and seaweed based treatments.

DETAILED DESCRIPTION

Many plants may benefit from the application of liquid compositions that provide a bio-stimulatory effect. Non-limiting examples of plant families that can benefit from such compositions can comprise: Solanaceae, Fabaceae (Leguminosae), Poaceae, Roasaceae, Vitaceae, Brassicaeae (Cruciferae), Caricaceae, Malvaceae, Sapindaceae, Anacardiaceae, Rutaceae, Moraceae, Convolvulaceae, Lamiaceae, Verbenaceae, Pedaliaceae, Asteraceae (Compositae), Apiaceae (Umbelliferae), Araliaceae, Oleaceae, Ericaceae, Actinidaceae, Cactaceae, Chenopodiaceae, Polygonaceae, Theaceae, Lecythidaceae, Rubiaceae, Papveraceae, Illiciaceae Grossulariaceae, Myrtaceae, Juglandaceae, Bertulaceae, Cucurbitaceae, Asparagaceae (Liliaceae), Alliaceae (Liliceae), Bromeliaceae, Zingieraceae, Muscaceae, Areaceae, Dioscoreaceae, Myristicaceae, Annonaceae, Euphorbiaceae, Lauraceae, Piperaceae, and Proteaceae.

The Solanaceae plant family includes a large number of agricultural crops, medicinal plants, spices, and ornamentals in it's over 2,500 species. Taxonomically classified in the Plantae kingdom, Tracheobionta (subkingdom), Spermatophyta (superdivision), Magnoliophyta (division), Manoliopsida (class), Asteridae (subclass), and Solanales (order), the Solanaceae family includes, but is not limited to, potatoes, tomatoes, eggplants, various peppers, tobacco, and petunias. Plants in the Solanaceae can be found on all the continents, excluding *Antarctica*, and thus have a widespread importance in agriculture across the globe.

The Fabaceae plant family (also known as the Leguminosae) comprises the third largest plant family with over 18,000 species, including a number of important agricultural and food plants. Taxonomically classified in the Plantae kingdom, Tracheobionta (subkingdom), Spermatophyta (superdivision), Magnoliophyta (division), Manoliopsida (class), Rosidae (subclass), and Fabales (order), the Fabaceae family includes, but is not limited to, soybeans, beans, green beans, peas, chickpeas, alfalfa, peanuts, sweet peas, carob, and liquorice. Plants in the Fabaceae family can range in size and type, including but not limited to, trees, small annual herbs, shrubs, and vines, and typically develop legumes. Plants in the Fabaceae family can be found on all the continents, excluding *Antarctica*, and thus have a widespread importance in agriculture across the globe. Besides food, plants in the Fabaceae family can be used to produce natural gums, dyes, and ornamentals.

The Poaceae plant family supplies food, building materials, and feedstock for fuel processing. Taxonomically classified in the Plantae kingdom, Tracheobionta (subkingdom), Spermatophyta (superdivision), Magnoliophyta (division), Liliopsida (class), Commelinidae (subclass), and Cyperales (order), the Poaceae family includes, but is not limited to, flowering plants, grasses, and cereal crops such as barely, corn, lemongrass, millet, oat, rye, rice, wheat, sugarcane, and sorghum. Types of turf grass found in Arizona include, but are not limited to, hybrid Bermuda grasses (e.g., 328 tifgrn, 419 tifway, tif sport).

The Rosaceae plant family includes flowering plants, herbs, shrubs, and trees. Taxonomically classified in the Plantae kingdom, Tracheobionta (subkingdom), Spermatophyta (superdivision), Magnoliophyta (division), Magnoliopsida (class), Rosidae (subclass), and Rosales (order), the Rosaceae family includes, but is not limited to, almond, apple, apricot, blackberry, cherry, nectarine, peach, plum, raspberry, strawberry, and quince.

The Vitaceae plant family includes flowering plants and vines. Taxonomically classified in the Plantae kingdom, Tracheobionta (subkingdom), Spermatophyta (superdivision), Magnoliophyta (division), Magnoliopsida (class), Rosidae (subclass), and Rhammales (order), the Vitaceae family includes, but is not limited to, grapes.

Particularly important in the production of fruit from plants is the beginning stage of growth where the plant emerges and matures into establishment. A method of treating a seed, seedling, or plant to directly improve the germination, emergence, and maturation of the plant; or to indirectly enhance the microbial soil community surrounding the seed or seedling is therefore valuable starting the plant on the path to marketable production. The standard typically used for assessing emergence is the achievement of the hypocotyl stage, where a stem is visibly protruding from the soil. The standard typically used for assessing maturation is the achievement of the cotyledon stage, where two leaves visibly form on the emerged stem.

Also important in the production of fruit from plants is the yield and quality of fruit, which may be quantified as the number, weight, color, firmness, ripeness, moisture, degree of insect infestation, degree of disease or rot, and degree of sunburn of the fruit. A method of treating a plant to directly improve the characteristics of the plant, or to indirectly enhance the chlorophyll level of the plant for photosynthetic capabilities and health of the plant's leaves, roots, and shoot to enable robust production of fruit is therefore valuable in increasing the efficiency of marketable production. Marketable and unmarketable designations may apply to both the plant and fruit, and may be defined differently based on the end use of the product, such as but not limited to, fresh market produce and processing for inclusion as an ingredient in a composition. The marketable determination may assess such qualities as, but not limited to, color, insect damage, blossom end rot, softness, and sunburn. The term total production may incorporate both marketable and unmarketable plants and fruit. The ratio of marketable plants or fruit to unmarketable plants or fruit may be referred to as utilization and expressed as a percentage. The utilization may be used as an indicator of the efficiency of the agricultural process as it shows the successful production of marketable plants or fruit, which will be obtain the highest financial return for the grower, whereas total production will not provide such an indication.

To achieve such improvements in emergence, maturation, and yield of plants, the inventors developed a method to treat such seeds and plants, and soil with a low concentration microalgae based composition, in a dried or liquid solution form. In some embodiments, the microalga comprises species of *Haematococcus*. *Haematococcus pluvialis* may be grown in mixotrophic and phototrophic conditions. Culturing *Haematococcus* in mixotrophic conditions comprises supplying light and organic carbon (e.g., acetic acid, acetate, glucose) to cells in an aqueous culture medium comprising trace metals and nutrients (e.g., nitrogen, phosphorus). Culturing *Haematococcus* in phototrophic conditions comprises supplying light and inorganic carbon (e.g., carbon dioxide) to cells in an aqueous culture medium comprising trace metals and nutrients (e.g., nitrogen, phosphorus). *Haematococcus* cells may experience multiple stages during a culture life, such as a motile stage where cell division occurs and Chlorophyll is a dominant pigment, a non-motile stage where the mass of the cells increases, and a non-motile stage where astaxanthin is accumulated. The different culture stages may comprise different culture media, such as a full nutrient media during the growth and motility stage, and a nutrient deplete media in the non-motile and astaxanthin accumulation stage.

In some embodiments, the *Haematococcus* cells may be harvested from a culture and used as whole cells in a liquid composition for application to seeds and plants, while in other embodiments the harvested *Haematococcus* cells may subjected to downstream processing and the resulting biomass or extract may be used in a dried composition (e.g., powder, pellet) or a liquid composition (e.g., suspension, solution) for application to plants, soil, or a combination thereof. Non-limiting examples of downstream processing comprise: drying the cells, lysing the cells, and subjecting the harvested cells to a solvent or supercritical carbon dioxide extraction process to isolate an astaxanthin containing oleo resin. In some embodiments, the extracted (i.e., residual) biomass remaining from an oleo resin extraction process may be used alone or in combination with other microalgae or extracts in a liquid composition for application to plants, soil, or a combination thereof. By subjecting the *Haematococcus* to an extraction process the resulting biomass is transformed from a natural whole state to a lysed condition where the cell is missing a significant amount of the natural components, thus differentiating the extracted *Haematococcus* biomass from that which is found in nature.

*Haematococcus pluvialis* biomass which had been subjected to being drum dried, mechanically lysed, and a supercritical carbon dioxide extraction process was analyzed for phytohormones content and compared to a commercial available seaweed extract product (Acadian Seaplants Limited, Nova Scotia, Canada) and PhycoTerra, a commercially available product comprising 10% solids of mixotrophic *Chlorella* (Heliae Development, LLC, Gilbert, Ariz.). The comparison is show in FIG. 1. The comparison shows that the extracted *Haematococcus* biomass had higher amounts of ABA and ABA metabolites than the commercially available products. The amount of cytokinins in the extracted *Haematococcus* was comparable to the PhycoTerra product and higher than the Acadian product. The amount of Auxins (IAA) and Salicylates in the extracted *Haematococcus* biomass was comparable with the Acadian product and higher than the PhycoTerra product.

Analysis of the DNA sequence of the strain of *Chlorella* found in the PhycoTerra product in the NCBI 18s rDNA reference database at the Culture Collection of Algae at the University of Cologne (CCAC) showed substantial similarity (i.e., greater than 95%) with multiple known strains of *Chlorella* and *Micractinium*. Those of skill in the art will recognize that *Chlorella* and *Micractinium* appear closely related in many taxonomic classification trees for microalgae, and strains and species may be re-classified from time to time. Thus for references throughout the instant specification for *Chlorella*, it is recognized that microalgae strains in related taxonomic classifications with similar characteristics to the reference PhycoTerra *Chlorella* strain would reasonably be expected to produce similar results.

Multiple samples of *Haematococcus pluvialis* biomass which had been subjected to being drum dried, mechanically lysed, and a supercritical carbon dioxide extraction process was also analyzed for macronutrient and micronutrient levels. The results of the analysis are shown in Table 1.

TABLE 1

|  | Extracted *Haematococcus* Sample 1 | Theoretical equivalent of sample 1 at 10% solids | Extracted *Haematococcus* Sample 2 | Theoretical equivalent of sample 2 at 10% solids |
| --- | --- | --- | --- | --- |
| Nitrogen (%) | 6.3 | 0.63 | 6.3 | 0.63 |
| Phosphorus (%) | 2.3 | 0.23 | 2.2 | 0.22 |
| Potassium (%) | 0.5 | 0.05 | 0.4 | 0.04 |
| Nitrogen (ppm) | 63260.8 | 6326.08 | 63169.6 | 6316.96 |
| Phosphorus (ppm) | 23100 | 2310 | 22000 | 2200 |
| Potassium (ppm) | 5120 | 512 | 4470 | 447 |
| Calcium (ppm) | 6680 | 668 | 6210 | 621 |
| Iron (ppm) | 2640 | 264 | 2700 | 270 |
| Magnesium (ppm) | 3060 | 306 | 2720 | 272 |
| Manganese (ppm) | 321 | 32.1 | 317 | 31.7 |
| Zinc (ppm) | 49 | 4.9 | 58.6 | 5.86 |

In some embodiments, *Haematococcus* may be the dominate microalgae species in the composition. In some embodiments, the microalgae population of the composition may comprise substantially extracted *Haematococcus* biomass. In some embodiments, *Haematococcus* comprises at least 99% of the microalgae population of the composition. In some embodiments, *Haematococcus* comprises at least 95% of the microalgae population of the composition. In some embodiments, *Haematococcus* comprises at least 90% of the microalgae population of the composition. In some embodiments, *Haematococcus* comprises at least 80% of the microalgae population of the composition. In some embodiments, *Haematococcus* comprises at least 70% of the microalgae population of the composition. In some embodiments, *Haematococcus* comprises at least 60% of the microalgae population of the composition. In some embodiments, *Haematococcus* comprises at least 50% of the microalgae population of the composition. In some embodiments, *Haematococcus* comprises at least 40% of the microalgae population of the composition. In some embodiments, *Haematococcus* comprises at least 30% of the microalgae population of the composition. In some embodiments, *Haematococcus* comprises at least 20% of the microalgae population of the composition. In some embodiments, *Haematococcus* comprises at least 10% of the microalgae population of the composition. In some embodiments, *Haematococcus* comprises at least 5% of the microalgae population of the composition. In some embodiments, *Haematococcus* comprises at least 1% of the microalgae population of the composition. In some embodiments, the composition lacks any detectable amount of any other microalgae species other than *Haematococcus*.

In some embodiments, *Haematococcus* cells may also be mixed with extracts from other plants, microalgae, macroalgae, seaweeds, and kelp. Non-limiting examples of seaweeds/macroalgae that may be processed through extraction and combined with microalgae cells may comprise species of *Kappaphycus, Ascophyllum, Macrocystis, Fucus, Laminaria, Sargassum, Turbinaria*, and *Durvilea*. In further embodiments, the extracts may comprise, but are not limited to, liquid extract from a species of *Kappaphycus*. In some embodiments, the extracts may comprise 50% or less by volume of the composition. In some embodiments, the extracts may comprise 40% or less by volume of the composition. In some embodiments, the extracts may comprise 30% or less by volume of the composition. In some embodiments, the extracts may comprise 20% or less by volume of the composition. In some embodiments, the extracts may comprise 10% or less by volume of the composition. In some embodiments, the extracts may comprise 5% or less by volume of the composition. In some embodiments, the extracts may comprise 4% or less by volume of the composition. In some embodiments, the extracts may comprise 3% or less by volume of the composition. In some embodiments, the extracts may comprise 2% or less by volume of the composition. In some embodiments, the extracts may comprise 1% or less by volume of the composition.

In some embodiments, *Haematococcus* cells may also be mixed with other types of microalgae, such as but not limited to *Chlorella*, to make a composition that is beneficial when applied to plants or soil. Non-limiting examples of microalgae species that can be used in the compositions and methods of the present invention include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella Candida, Chlorella capsulate, Chlorella desiccate, Chlorella ellipsoidea, Chlorella emersonii, Chlorella fusca, Chlorella fusca* var. *vacuolate, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena* spp., *Franceia* sp., *Fragilaria crotonensis, Fragilaria* sp., *Gleocapsa* sp., *Gloeothamnion* sp., *Haematococcus pluvialis, Hymenomonas* sp., *Isochrysis aff. galbana, Isochrysis galbana, Lepocinclis, Micractinium, Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrina, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricornutum, Phagus, Phormidium, Platymonas* sp., *Pleurochrysis camerae, Pleurochrysis dentate, Pleurochrysis* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocys-*

*tisf, Tagetes erecta, Tagetes patula, Tetraedron, Tetraselmis* sp., *Tetraselmis suecica, Thalassiosira weissflogii,* and *Viridiella fridericiana*.

In some embodiments, the non-*Haematococcus* types of microalgae may comprise 1-99% of the microalgae species in the composition for application to plants. In some embodiments, non-*Haematococcus* microalgae may comprise at least 99% of the microalgae population of the composition. In some embodiments, non-*Haematococcus* microalgae may comprise at least 95% of the microalgae population of the composition. In some embodiments, non-*Haematococcus* microalgae may comprise at least 90% of the microalgae population of the composition. In some embodiments, non-*Haematococcus* microalgae may comprise at least 80% of the microalgae population of the composition. In some embodiments, non-*Haematococcus* microalgae may comprise at least 70% of the microalgae population of the composition. In some embodiments, non-*Haematococcus* microalgae may comprise at least 60% of the microalgae population of the composition. In some embodiments, non-*Haematococcus* microalgae may comprise at least 50% of the microalgae population of the composition. In some embodiments, non-*Haematococcus* microalgae may comprise at least 40% of the microalgae population of the composition. In some embodiments, non-*Haematococcus* microalgae may comprise at least 30% of the microalgae population of the composition. In some embodiments, non-*Haematococcus* microalgae may comprise at least 20% of the microalgae population of the composition. In some embodiments, non-*Haematococcus* microalgae may comprise at least 10% of the microalgae population of the composition. In some embodiments, non-*Haematococcus* microalgae may comprise at least 5% of the microalgae population of the composition. In some embodiments, non-*Haematococcus* microalgae may comprise at least 1% of the microalgae population of the composition.

In one embodiment, *Chlorella* sp. may be cultured in mixotrophic conditions, which comprises a culture medium primary comprised of water with trace nutrients (e.g., nitrates, phosphates, vitamins, metals found in BG-11 recipe (available from UTEX The Culture Collection of Algae at the University of Texas at Austin, Austin, Tex.)), light as an energy source for photosynthesis, organic carbon (e.g., acetate, acetic acid) as both an energy source and a source of carbon. In some embodiments, the culture media may comprise BG-11 media or a media derived from BG-11 culture media (e.g., in which additional component(s) are added to the media and/or one or more elements of the media is increased by 5%, 10%, 15%, 20%, 25%, 33%, 50%, or more over unmodified BG-11 media). In some embodiments, the *Chlorella* may be cultured in non-axenic mixotrophic conditions in the presence of contaminating organisms, such as but not limited to bacteria. Methods of culturing such microalgae in non-axenic mixotrophic conditions may be found in WO2014/074769A2 (Ganuza, et al.), hereby incorporated by reference.

By artificially controlling aspects of the *Chlorella* culturing process such as the organic carbon feed (e.g., acetic acid, acetate), oxygen levels, pH, and light, the culturing process differs from the culturing process that *Chlorella* experiences in nature. In addition to controlling various aspects of the culturing process, intervention by human operators or automated systems occurs during the non-axenic mixotrophic culturing of *Chlorella* through contamination control methods to prevent the *Chlorella* from being overrun and outcompeted by contaminating organisms (e.g., fungi, bacteria). Contamination control methods for microalgae cultures are known in the art and such suitable contamination control methods for non-axenic mixotrophic microalgae cultures are disclosed in WO2014/074769A2 (Ganuza, et al.), hereby incorporated by reference. By intervening in the microalgae culturing process, the impact of the contaminating microorganisms can be mitigated by suppressing the proliferation of containing organism populations and the effect on the microalgal cells (e.g., lysing, infection, death, clumping). Thus through artificial control of aspects of the culturing process and intervening in the culturing process with contamination control methods, the *Chlorella* culture produced as a whole and used in the described inventive compositions differs from the culture that results from a *Chlorella* culturing process that occurs in nature.

During the mixotrophic culturing process the *Chlorella* culture may also comprise cell debris and compounds excreted from the *Chlorella* cells into the culture medium. The output of the *Chlorella* mixotrophic culturing process provides the active ingredient for composition that is applied to plants for improving yield and quality without separate addition to or supplementation of the composition with other active ingredients not found in the mixotrophic *Chlorella* whole cells and accompanying culture medium from the mixotrophic culturing process such as, but not limited to: non-*Chlorella* microalgae cells, microalgae extracts, macroalgae, macroalgae extracts, liquid fertilizers, granular fertilizers, mineral complexes (e.g., calcium, sodium, zinc, manganese, cobalt, silicon), fungi, bacteria, nematodes, protozoa, digestate solids, chemicals (e.g., ethanolamine, borax, boric acid), humic acid, nitrogen and nitrogen derivatives, phosphorus rock, pesticides, herbicides, insecticides, enzymes, plant fiber (e.g., coconut fiber).

In some embodiments, the mixotrophic *Chlorella* may be previously frozen and thawed before inclusion in the liquid composition. In some embodiments, the mixotrophic *Chlorella* may not have been subjected to a previous freezing or thawing process. In some embodiments, the mixotrophic *Chlorella* whole cells have not been subjected to a drying process. The cell walls of the mixotrophic *Chlorella* of the composition have not been lysed or disrupted, and the mixotrophic *Chlorella* cells have not been subjected to an extraction process or process that pulverizes the cells. The mixotrophic *Chlorella* whole cells are not subjected to a purification process for isolating the mixotrophic *Chlorella* whole cells from the accompanying constituents of the culturing process (e.g., trace nutrients, residual organic carbon, bacteria, cell debris, cell excretions), and thus the whole output from the mixotrophic *Chlorella* culturing process comprising whole *Chlorella* cells, culture medium, cell excretions, cell debris, bacteria, residual organic carbon, and trace nutrients, is used in the liquid composition for application to plants. In some embodiments, the mixotrophic *Chlorella* whole cells and the accompanying constituents of the culturing process are concentrated in the composition. In some embodiments, the mixotrophic *Chlorella* whole cells and the accompanying constituents of the culturing process are diluted in the composition to a low concentration. The mixotrophic *Chlorella* whole cells of the composition are not fossilized. In some embodiments, the mixotrophic *Chlorella* whole cells are not maintained in a viable state in the composition for continued growth after the method of using the composition in a soil or foliar application. In some embodiments, the mixotrophic *Chlorella* base composition may be biologically inactive after the composition is prepared. In some embodiments, the mixotrophic *Chlorella* base composition may be substantially biologically inactive after the composition is prepared. In some embodiments, the mixotrophic *Chlorella* base composition may increase in biological activity after the prepared composition is exposed to air.

In some embodiments, a liquid composition may comprise low concentrations of bacteria contributing to the solids percentage of the composition in addition to the whole mixotrophic *Chlorella* cells. Examples of bacteria found in non-axenic mixotrophic conditions may be found in WO2014/074769A2 (Ganuza, et al.), hereby incorporated by reference. A live bacteria count may be determined using methods known in the art such as plate counts, plates counts using Petrifilm available from 3M (St. Paul, Minn.), spectrophotometric (turbidimetric) measurements, visual comparison of turbidity with a known standard, direct cell counts under a microscope, cell mass determination, and measurement of cellular activity. Live bacteria counts in a non-axenic mixotrophic microalgae culture may range from $10^4$ to $10^9$ CFU/mL, and may depend on contamination control measures taken during the culturing of the microalgae. The level of bacteria in the composition may be determined by an aerobic plate count which quantifies aerobic colony forming units (CFU) in a designated volume. In some embodiments, the composition comprises an aerobic plate count of 40,000-400,000 CFU/mL. In some embodiments, the composition comprises an aerobic plate count of 40,000-100,000 CFU/mL. In some embodiments, the composition comprises an aerobic plate count of 100,000-200,000 CFU/mL. In some embodiments, the composition comprises an aerobic plate count of 200,000-300,000 CFU/mL. In some embodiments, the composition comprises an aerobic plate count of 300,000-400,000 CFU/mL.

In some embodiments, the microalgae based composition can be supplemented with a supplemental nutrient such as nitrogen, phosphorus, or potassium to increase the levels within the composition to at least 1% of the total composition (i.e., addition of N, P, or K to increase levels at least 1-0-0, 0-1-0, 0-0-1, or combinations thereof). In some embodiments, the microalgae composition may be supplemented with nutrients such as, but not limited to, calcium, magnesium, silicon, sulfur, iron, manganese, zinc, copper, boron, molybdenum, chlorine, sodium, aluminum, vanadium, nickel, cerium, dysprosium, erbium, europium, gadolinium, holmium, lanthanum, lutetium, neodymium, praseodymium, promethium, samarium, scandium, terbium, thulium, ytterbium, and yttrium. In some embodiments, the supplemented nutrient is not uptaken, chelated, or absorbed by the microalgae. In some embodiments, the concentration of the supplemental nutrient may comprise 1-50 g per 100 g of the composition.

A liquid composition comprising microalgae may be stabilized by heating and cooling in a pasteurization process. As shown in the Examples, the inventors found that the active ingredients of the *Haematococcus* based composition maintained effectiveness in improving plant germination, emergence, maturation, and yield when applied to Solanaceae plants after being subjected to the heating and cooling of a pasteurization process. In other embodiments, liquid compositions with whole cells or processed cells (e.g., dried, lysed, extracted) of *Haematococcus* cells may not need to be stabilized by pasteurization. For example, a phototrophic culture of *Haematococcus* or cells that have been processed, such as by drying, lysing, and extraction, may comprise such low levels of bacteria that a liquid composition may remain stable without being subjected to the heating and cooling of a pasteurization process.

In some embodiments, the composition may be heated to a temperature in the range of 50-70° C. In some embodiments, the composition may be heated to a temperature in the range of 55-65° C. In some embodiments, the composition may be heated to a temperature in the range of 58-62° C. In some embodiments, the composition may be heated to a temperature in the range of 50-60° C. In some embodiments, the composition may be heated to a temperature in the range of 60-70° C.

In some embodiments, the composition may be heated for a time period in the range of 90-150 minutes. In some embodiments, the composition may be heated for a time period in the range of 110-130 minutes. In some embodiments, the composition may be heated for a time period in the range of 90-100 minutes. In some embodiments, the composition may be heated for a time period in the range of 100-110 minutes. In some embodiments, the composition may be heated for a time period in the range of 110-120 minutes. In some embodiments, the composition may be heated for a time period in the range of 120-130 minutes. In some embodiments, the composition may be heated for a time period in the range of 130-140 minutes. In some embodiments, the composition may be heated for a time period in the range of 140-150 minutes.

After the step of heating or subjecting the liquid composition to high temperatures is complete, the compositions may be cooled at any rate to a temperature that is safe to work with. In one non-limiting embodiment, the composition may be cooled to a temperature in the range of 35-45° C. In some embodiments, the composition may be cooled to a temperature in the range of 36-44° C. In some embodiments, the composition may be cooled to a temperature in the range of 37-43° C. In some embodiments, the composition may be cooled to a temperature in the range of 38-42° C. In some embodiments, the composition may be cooled to a temperature in the range of 39-41° C. In further embodiments, the pasteurization process may be part of a continuous production process that also involves packaging, and thus the liquid composition may be packaged (e.g., bottled) directly after the heating or high temperature stage without a cooling step.

In some embodiments, the composition may comprise 5-30% solids by weight of microalgae cells (i.e., 5-30 g of microalgae cells/100 mL of the liquid composition). In some embodiments, the composition may comprise 5-20% solids by weight of microalgae cells. In some embodiments, the composition may comprise 5-15% solids by weight of microalgae cells. In some embodiments, the composition may comprise 5-10% solids by weight of microalgae cells. In some embodiments, the composition may comprise 10-20% solids by weight of microalgae cells. In some embodiments, the composition may comprise 10-20% solids by weight of microalgae cells. In some embodiments, the composition may comprise 20-30% solids by weight of microalgae cells. In some embodiments, further dilution of the microalgae cells percent solids by weight may be occur before application for low concentration applications of the composition.

In some embodiments, the composition may comprise less than 1% solids by weight of microalgae cells (i.e., less than 1 g of microalgae cells/100 mL of the liquid composition). In some embodiments, the composition may comprise less than 0.9% solids by weight of microalgae cells. In some embodiments, the composition may comprise less than 0.8% solids by weight of microalgae cells. In some embodiments, the composition may comprise less than 0.7% solids by weight of microalgae cells. In some embodiments, the composition may comprise less than 0.6% solids by weight of microalgae cells. In some embodiments, the composition may comprise less than 0.5% solids by weight of microalgae cells. In some embodiments, the composition may comprise less than 0.4% solids by weight of microalgae cells. In some embodiments, the composition may comprise less than 0.3% solids by weight of microalgae cells. In some embodiments, the composition may comprise less than 0.2% solids by weight of microalgae cells. In some embodiments, the composition may comprise less than 0.1% solids by weight of microalgae cells. In some embodiments, the effective amount in an application of the liquid composition for enhanced germination, emergence, or maturation may comprise a concentration of solids of microalgae cells in the range of 0.002642-0.079252% (i.e., about 0.003% to about 0.080%, or about 0.003 g/100 mL to about 0.080 g/100 mL), equivalent to a diluted concentration of 2-10 mL/gallon of a solution with an original percent solids of microalgae cells in the range of 5-30%.

In some embodiments, stabilizing means that are not active regarding the improvement of plant germination, emergence, maturation, quality, and yield, but instead aid in stabilizing the composition may be added to prevent the proliferation of unwanted microorganisms (e.g., yeast, mold) and prolong shelf life. Such inactive but stabilizing means may comprise an acid, such as but not limited to phosphoric acid, and a yeast and mold inhibitor, such as but not limited to potassium sorbate. In some embodiments, the stabilizing means are suitable for plants and do not inhibit the growth or health of the plant. In the alternative, the stabilizing means may contribute to nutritional properties of the liquid composition, such as but not limited to, the levels of nitrogen, phosphorus, or potassium.

In some embodiments, the composition may comprise less than 0.3% phosphoric acid. In some embodiments, the composition may comprise 0.01-0.3% phosphoric acid. In some embodiments, the composition may comprise 0.05-0.25% phosphoric acid. In some embodiments, the composition may comprise 0.01-0.1% phosphoric acid. In some embodiments, the composition may comprise 0.1-0.2% phosphoric acid. In some embodiments, the composition may comprise 0.2-0.3% phosphoric acid.

In some embodiments, the composition may comprise less than 0.5% potassium sorbate. In some embodiments, the composition may comprise 0.01-0.5% potassium sorbate. In some embodiments, the composition may comprise 0.05-0.4% potassium sorbate. In some embodiments, the composition may comprise 0.01-0.1% potassium sorbate. In some embodiments, the composition may comprise 0.1-0.2% potassium sorbate. In some embodiments, the composition may comprise 0.2-0.3% potassium sorbate. In some embodiments, the composition may comprise 0.3-0.4% potassium sorbate. In some embodiments, the composition may comprise 0.4-0.5% potassium sorbate.

In some embodiments, the composition is a liquid and substantially comprises of water. In some embodiments, the composition may comprise 70-95% water. In some embodiments, the composition may comprise 85-95% water. In some embodiments, the composition may comprise 70-75% water. In some embodiments, the composition may comprise 75-80% water. In some embodiments, the composition may comprise 80-85% water. In some embodiments, the composition may comprise 85-90% water. In some embodiments, the composition may comprise 90-95% water. The liquid nature and high water content of the composition facilitates administration of the composition in a variety of manners, such as but not limit to: flowing through an irrigation system, flowing through an above ground drip irrigation system, flowing through a buried drip irrigation system, flowing through a central pivot irrigation system, sprayers, sprinklers, and water cans.

In some embodiments, the liquid composition may be used immediately after formulation, or may be stored in containers for later use. In some embodiments, the composition may be stored out of direct sunlight. In some embodiments, the composition may be refrigerated. In some embodiments, the composition may be stored at 1-10° C. In some embodiments, the composition may be stored at 1-3° C. In some embodiments, the composition may be stored at 3-5° C. In some embodiments, the composition may be stored at 5-8° C. In some embodiments, the composition may be stored at 8-10° C.

In some embodiments, administration of the liquid composition to a seed or plant may be in an amount effective to produce an enhanced characteristic in plants compared to a substantially identical population of untreated seeds or plants. Such enhanced characteristics may comprise accelerated seed germination, accelerated seedling emergence, improved seedling emergence, improved leaf formation, accelerated leaf formation, improved plant maturation, accelerated plant maturation, increased plant yield, increased plant growth, increased plant quality, increased plant health, increased fruit yield, increased fruit growth, and increased fruit quality. Non-limiting examples of such enhanced characteristics may comprise accelerated achievement of the hypocotyl stage, accelerated protrusion of a stem from the soil, accelerated achievement of the cotyledon stage, accelerated leaf formation, increased marketable plant weight, increased marketable plant yield, increased marketable fruit weight, increased production plant weight, increased production fruit weight, increased utilization (indicator of efficiency in the agricultural process based on ratio of marketable fruit to unmarketable fruit), increased chlorophyll content (indicator of plant health), increased plant weight (indicator of plant health), increased root weight (indicator of plant health), and increased shoot weight (indicator of plant health). Such enhanced characteristics may occur individually in a plant, or in combinations of multiple enhanced characteristics.

In some embodiments, after harvest of the microalgae from the culturing vessel, the microalgae may be dried or dehydrated to form a composition of dried microalgae cells (i.e., reduced moisture content). The microalgae cells may be dried by at least one method selected from the group consisting of: freeze drying (or lypohilization), drum (or rotary) drying, spray drying, crossflow air drying, solar drying, vacuum shelf drying, pulse combustion drying, flash drying, furnace drying, belt conveyor drying, and refractance window drying. In some embodiments, the microalgae cells may be dried by a combination of two or more methods, such as in a process with multiple drying methods in series. The process of drying the microalgae may reduce the percent moisture (on a wet basis) to the range of about 1-15% and result in a cake, flakes, or a powder, which is more uniform and more stable than the wet culture of microalgae. In some embodiments, the dried microalgae cells may be intact. In some embodiments, the dried microalgae cells may be lysed or disrupted. In some embodiments, the microalgae cells may be lysed or disrupted prior to or after drying by mechanical, electrical, acoustic, or chemical means. In some embodiments, drying the microalgae cells achieves an acceptable product stability for storage, with the reduction or elimination of chemical stabilizers. The composition may be stored in any suitable container such as, but not limited to, a bag, bucket, jug, tote, or bottle.

In some embodiments, the dried microalgae cells may have a moisture content of 1-15% on a wet basis. In some embodiments, the dried microalgae cells may have a moisture content of 1-2% on a wet basis. In some embodiments, the dried microalgae cells may have a moisture content of 2-3% on a wet basis. In some embodiments, the dried microalgae cells may have a moisture content of 3-5% on a wet basis. In some embodiments, the dried microalgae cells may have a moisture content of 5-7% on a wet basis. In some embodiments, the dried microalgae cells may have a moisture content of 7-10% on a wet basis. In some embodiments, the dried microalgae cells may have a moisture content of 10-12% on a wet basis. In some embodiments, the dried microalgae cells may have a moisture content of 12-15% on a wet basis. In some embodiments, the dried microalgae cells may have a moisture content of 1-8% on a wet basis. In some embodiments, the dried microalgae cells may have a moisture content of 8-15% on a wet basis.

The various drying processes may have different capabilities such as, but not limited to, the amount of moisture that may be removed, the preservation of metabolites (e.g., proteins, lipids, pigments, carbohydrates, polysaccharides, soluble nitrogen, phytohormones), and the effect on the cell wall or membrane. For example, loss of protein in *Spirulina* biomass has been found to increase proportionally as the drying temperature increases. Additionally, drying at high temperatures has been shown to alter polymer chains, alter interactions between polysaccharide and glycoprotein, and increase bound water content of polysaccharides. Pigments and fatty acids are also known to oxidize and de-stabilize to different degrees in different drying processes. The effectiveness of each drying method may also vary based on the microalgae species due to different physical characteristics of the microalgae (e.g., sheer sensitivity, cell size, cell wall thickness and composition). The method of drying and drying method parameters may also result in a structural change to the microalgae cell such as, but not limited to, increased porosity in the cell wall, changes in the cell wall make up or bonds, and measurable changes in cell characteristics (e.g., elasticity, viscosity, digestibility); as wells as functional differences when applied to plants that can be measured in changes in plant performance or plant characteristics. Drying microalgae with a combination of methods in series may also result in structural and functional changes, minimize structural and functional changes, or increase the effectiveness for a particular type of microalgae.

Drum drying comprises the use of sloped, rotating cylinders which use gravity to move the microalgal biomass from one end to the other. Drum drying may be conducted with direct contact between a hot gas and the microalgal biomass, or indirect heating in which the gas and microalgal biomass is separated by a barrier such as a steel shell. An example of a drum drying process for *Scenedesmus* may comprise 10 seconds of heating at 120° C. Possible effects to the microalga biomass in a drum drying process include sterilization of the biomass, and breaking of the cell wall. Microalgal biomass that is drum dried may have higher digestibility than microalgal biomass that is spray dried.

Freeze drying comprises freezing the microalgal biomass and then transferring the frozen biomass to a vacuum chamber with reduced pressure (e.g., 4.6 Torr). The ice in the microalgal biomass changes to vapor through sublimation which is collected on an extremely cold condenser and removed from the vacuum chamber. Freeze drying typically minimizes the degradation of unsaturated fatty acids and pigments (e.g., carotenoids) through oxidation, which preserves the nutritional value of the microalgal biomass. Although the targeted removal of water in the freeze drying process is beneficial, the process is very costly and time consuming which makes freeze drying impractical for many commercial applications. In some embodiments, microalgae dried by freeze drying may comprise 2-6% moisture (on a wet basis). An example of a freeze drying process for *Scenedesmus* may comprise 24 hours at −84° C. Freeze drying is known to maintain the integrity of the microalgal cell, but is also known been known in some cases to disrupt the cell or increase the pore size in the cell wall. In *Scenedesmus*, freeze drying was found to decrease rigidity, increase surface area by 165%, and increase pore size by 19% of the cells (see eSEM images below). In *Phaeodactylum ricornutum*, freeze drying had no effect on the total lipid content, made the cells more susceptible to lipolysis (i.e., breakdown of lipids, hydrolysis of triglycerides into glycerol and free fatty acids) upon storage than spray dried cells, and made the cells less susceptible to oxidation than spray dried cells.

Spray drying comprises atomizing an aqueous microalgae culture into droplets sprayed downwardly in a vertical tower through which hot gases pass downward. The gas stream may be exhausted through a cyclonic separator. The process of spray drying is expensive, but slightly cheaper than freeze drying. Spray drying has become the method of choice for high value products (>$1,000/ton). With the proper type of burner, oxygen can be virtually eliminated from the recycled drying gas, which prevents the oxidation of oxygen sensitive products (e.g., carotenoids). In some embodiments, microalgae dried by spray drying may comprise 1-7% moisture (on a wet basis). Examples of spray drying systems include: box dryers, tall-form spray dryers, fluidized bed dryers, and moving fluidized bed dryers (e.g., FilterMat spray dryer GEA Process Engineering Inc.). An open cycle spray dryer with a particular direct fired air heater may operate at elevated temperatures (e.g., 60-93° C.) and high oxygen concentrations (e.g., 19-20%). The possible effects of spray drying on microalgal biomass include rupturing the cells walls, reduction of protein content by 10-15%, significant deterioration of pigments (depending on the oxygen concentration), and a lower digestibility than drum drying. In *Phyaeodactylum ricornutum*, spray drying had no effect on the total lipid content, made the cells less susceptible to lipolysis than freeze drying, and made the cells more susceptible to oxidation than freeze drying (possibly due to the breakdown of protective carotenoids).

Crossflow air drying uses movement of heated air across a layer of microalgae on a tray, which is a modification of indirect solar and convection oven driers. Crossflow air drying is faster than solar drying, cheaper than drum drying, and is known to typically not break the microalgal cell wall. In some embodiments, microalgae dried by crossflow air drying may comprise 8-12% moisture (on a wet basis). Examples of crossflow air drying for *Spirulina* may comprise: 1) a temperature of 62° C. for 14 hours, 2) a temperature of 50-60° C., a relative humidity of 7-10%, an air velocity of 1.5 m/s, and a duration of 150-220 minutes, 3) a temperature of 40-60° C. and an air velocity of 1.9-3.8 m/s, and 4) temperatures of 50-70° C. for layers of 3-7 mm in a perforated tray with parallel air flow. Crossflow air drying of *Spirulina* has shown a loss in protein of about 17% and a loss in phycocyanin of 37-50%. Particularly, degradation of phycocyanin was found to occur above 60° C., but there was no significant change in the fatty acid composition in the crossflow air drying methods.

Examples of crossflow air drying of *Chlorella* kessleri and *Chlamydomonas reinhardtii* may comprise a temperature of 55° C. for more than 5 hours. Crossflow air drying of *Chlorella* kessleri and *Chlamydomonas reinhardtii* has produced a reduction of chlorophyll relative to the dry cell weight, an increase of total fatty acid content relative to the dry cell, a decrease of polar lipids relative to the dry cell weight, and a decrease in the availability of nutritional salts (e.g., S, N). A cell's sensitivity to air drying stress (as measured through the change in chlorophyll) may be correlated to the properties of the cell wall. For example, the crossflow air dried *Chlamydomonas reinhardtii* (hydroxyproline-rich glucoprotein based cell walls) had a larger decrease in chlorophyll than the *Chlorella* kessleri (sugar based cell walls), which may be associated with the cell wall's ability to restructure in S and N deficient conditions. In an example of drying 5-7 mm thick layers of *Aphanothece microscopia Nageli* at temperatures of 40-60° C. with parallel air flow of 1.5 m/s, it was found that drying conditions influenced the concentrations of protein, carbohydrates, and lipids in the biomass.

Solar drying methods may comprise the use of direct solar radiation to dry microalgae on sand or a plastic sheet, or the indirect use of solar radiation to heat air that is circulated around microalgae in a dryer. Direct solar drying is strongly weather dependent, slow, and may require a short duration of high heat (e.g., 120° C.) to increase the biological value of the microalgal biomass. An example of a direct solar drying process for *Scenedesmus* may comprise a 1,500 micron thickness white plastic drying bed liner, a temperature of 25-30° C., and a duration of 72 hours. The possible effects of direct solar drying on microalgal biomass include chlorophyll degradation, overheating of the biomass, and creation of an unpleasant odor. Indirect solar drying prevents overheating, has a higher drying rate than direct solar drying, but produces a less attractive profile in the final product. An indirect solar drying method for microalgae may comprise temperature of 65-70° C. for 0.5-6 hours.

Drying of a thin film of microalgal biomass in a convection oven is a fairly common practice performed in scientific literature to test the biomass going through further processing, but may be less practical for many commercial applications. Thin film convection oven drying has been demonstrated in the literature with species of *Chlorella*, *Chlamydomonas*, and *Scenedesmus*. In some embodiments, microalgae dried by oven drying may comprise 6-10% moisture (on a wet basis). Thin film convection oven drying methods may comprise temperatures of 30-90° C., and durations of 4-12 hours. Thin film convection oven dried microalgal biomass showed no significant change in the fatty acid profile and a slight decrease in the degree of unsaturation of fatty acids at higher temperature for ruptured cells (likely due to oxidation causing cleavage of unsaturated bonds).

Microalgae may be dried in thin layers with heat at a reduced pressure. Examples of drying of *Spirulina* in layers within a vacuum may comprise temperatures of 50-65° C. and a pressure of 0.05-0.06 atm. Possible effects on the microalgae that may result from vacuum shelf drying include development of a hygroscopic property (i.e., ability to attract and hold water particles from the surrounding environment by absorption or adsorption) and development of a porous structure.

Pulse combustion drying uses a blast of controlled heat to flash dry the microalgae. Air is pumped into a combustion chamber, mixed with a fuel and ignited to created pressurized hot gas (e.g., at 3 psi). The dryer may automatically blast the heated gas with quench air to control the temperature of the heated gas before coming into contact with the microalgae. The process is then repeated multiple times to provide the pulses of heated gas. Pulse combustion heating is known to dry microalgae at a low heat which preserves the integrity and nutritional value of the microalgae. Flash drying comprises spraying or injecting a mixture of dried and undried material into a hot gas stream, and is commonly used in wastewater sludge drying.

Drying of microalgae using an incinerator or furnace may comprise heating the biomass to a high temperature (e.g., 100° C.) to evaporate the water. The heating may be performed at a level below the temperature at which the microalgae will burn and may comprise using hot gases that proceed downwardly with the biomass in parallel flow. Microalgae that are dewatered to an appropriate solids level may be dried indirectly by heating elements lining the pathway of a belt conveyor. Refractance window drying is a dehydration method that uses infra-red light, rather than high direct temperature, to remove moisture from microalgae. Wet microalgae biomass may be translated through an evaporation chamber by a belt disposed above a circulating hot water reservoir to dry the microalgae with infra-red energy in a refractance window drying. In some embodiments, microalgae dried by refractance window drying may comprise 3-8% moisture (on a wet basis).

In some embodiments, the dry composition may be mixed with water and stabilized by heating and cooling in a pasteurization process, adjustment of pH, the addition of an inhibitor of yeast and mold growth, or combinations thereof. In one non-limiting example of preparing the dried microalgae composition for application to plants, the microalgae harvested from the culturing system is first held in a harvest tank before centrifuging the culture. Once the microalgae is centrifuged, the centrifuge discharges the fraction rich in microalgae whole cell solids, but also containing the accompanying constituents from the culture medium, into a container at a temperature of about 30° C. The microalgae composition is then dried.

Surprisingly, the inventors found that administration of the described composition in low concentration applications was effective in producing enhanced characteristics in plants. In some embodiments, a liquid composition may be administered before the seed is planted. In some embodiments, a liquid composition may be administered at the time the seed is planted. In some embodiments, a liquid composition may be administered after the seed is planted. In some embodiments, a liquid composition may be administered to plants that have emerged from the ground. In some embodiments, a dried composition may be applied to the soil before, during, or after the planting of a seed. In some embodiments, a dried composition may be applied to the soil before or after a plant emerges from the soil.

In some embodiments, administration of the composition may increase the number of plants emerged by 25-1,600% compared to a substantially identical population of untreated seeds of plants. In some embodiments, administration of the composition may increase the number of plants emerged by at least 25% compared to a substantially identical population of untreated seeds of plants. In some embodiments, administration of the composition may increase the number of plants emerged by at least 30% compared to a substantially identical population of untreated seeds of plants. In some embodiments, administration of the composition may increase the number of plants emerged by at least 40% compared to a substantially identical population of untreated seeds of plants. In some embodiments, administration of the composition may increase the number of plants emerged by at least 50% compared to a substantially identical population of untreated seeds of plants. In some embodiments, administration of the composition may increase the number of plants emerged by at least 60% compared to a substantially identical population of untreated seeds of plants. In some embodiments, administration of the composition may increase the number of plants emerged by at least 70% compared to a substantially identical population of untreated seeds of plants. In some embodiments, administration of the composition may increase the number of plants emerged by at least 80% compared to a substantially identical population of untreated seeds of plants. In some embodiments, administration of the composition may increase the number of plants emerged by at least 90% compared to a substantially identical population of untreated seeds of plants.

In some embodiments, administration of the composition may increase the number of plants emerged by at least 100% compared to a substantially identical population of untreated seeds of plants. In some embodiments, administration of the composition may increase the number of plants emerged by at least 200% compared to a substantially identical population of untreated seeds of plants. In some embodiments, administration of the composition may increase the number of plants emerged by at least 300% compared to a substantially identical population of untreated seeds of plants. In some embodiments, administration of the composition may increase the number of plants emerged by at least 400% compared to a substantially identical population of untreated seeds of plants. In some embodiments, administration of the composition may increase the number of plants emerged by at least 500% compared to a substantially identical population of untreated seeds of plants. In some embodiments, administration of the composition may increase the number of plants emerged by at least 600% compared to a substantially identical population of untreated seeds of plants. In some embodiments, administration of the composition may increase the number of plants emerged by at least 700% compared to a substantially identical population of untreated seeds of plants. In some embodiments, administration of the composition may increase the number of plants emerged by at least 800% compared to a substantially identical population of untreated seeds of plants. In some embodiments, administration of the composition may increase the number of plants emerged by at least 900% compared to a substantially identical population of untreated seeds of plants. In some embodiments, administration of the composition may increase the number of plants emerged by at least 1,000% compared to a substantially identical population of untreated seeds of plants. In some embodiments, administration of the composition may increase the number of plants emerged by at least 1,600% compared to a substantially identical population of untreated seeds of plants.

In some embodiments, the administration of the composition may increase utilization by 80-110% compared to a substantially identical population of untreated plants. In some embodiments, administration of the composition may increase utilization by at least 80% compared to a substantially identical population of untreated plants. In some embodiments, administration of the composition may increase utilization by at least 85% compared to a substantially identical population of untreated plants. In some embodiments, administration of the composition may increase utilization by at least 90% compared to a substantially identical population of untreated plants. In some embodiments, administration of the composition may increase utilization by at least 95% compared to a substantially identical population of untreated plants. In some embodiments, administration of the composition may increase utilization by at least 100% compared to a substantially identical population of untreated plants.

In some embodiments, the administration of the composition may increase marketable plant weight by 125-300% compared to a substantially identical population of untreated plants. In some embodiments, administration of the composition may increase the marketable plant weight by at least 125% compared to a substantially identical population of untreated plants. In some embodiments, administration of the composition may increase the marketable plant weight by at least 150% compared to a substantially identical population of untreated plants. In some embodiments, administration of the composition may increase the marketable plant weight by at least 175% compared to a substantially identical population of untreated plants. In some embodiments administration of the composition may increase the marketable plant weight by at least 200% compared to a substantially identical population of untreated plants. In some embodiments administration of the composition may increase the marketable plant weight by at least 225% compared to a substantially identical population of untreated plants. In some embodiments, administration of the composition may increase the marketable plant weight by at least 250% compared a substantially identical population of untreated plants. In some embodiments, administration of the composition may increase the marketable plant weight by at least 275% compared to a substantially identical population of untreated plants. In some embodiments, administration of the composition may increase the marketable plant weight by at least 300% compared to a substantially identical population of untreated plants.

In some embodiments, the administration of the composition may increase marketable plant yield by 100-200% compared to a substantially identical population of untreated plants. In some embodiments, administration of the composition may increase the marketable plant yield by at least 100% compared to a substantially identical population of untreated plants. In some embodiments, administration of the composition may increase the marketable plant yield by at least 125% compared to a substantially identical population of untreated plants. In some embodiments, administration of the composition may increase the marketable plant yield by at least 150% compared to a substantially identical population of untreated plants. In some embodiments, administration of the composition may increase the marketable plant yield by at least 175% compared to a substantially identical population of untreated plants. In some embodiments, administration of the composition may increase the marketable plant yield by at least 200% compared to a substantially identical population of untreated plants.

In some embodiments, the administration of the composition may increase marketable fruit weight by 10-75% compared to a substantially identical population of untreated plants. In some embodiments, administration of composition may increase the marketable fruit weight by at least 10% compared to a substantially identical population of untreated plants. In some embodiments, administration of composition may increase the marketable fruit weight by at least 25% compared to a substantially identical population of untreated plants. In some embodiments, administration of composition may increase the marketable fruit weight by at least 50% compared to a substantially identical population of untreated plants. In some embodiments, administration of composition may increase the marketable fruit weight by at least 60% compared to a substantially identical population of untreated plants. In some embodiments, administration of composition may increase the marketable fruit weight by at least 75% compared to a substantially identical population of untreated plants.

In some embodiments, the administration of the composition may increase production plant weight by 70-120% compared to a substantially identical population of untreated plants. In some embodiments, administration of composition may increase production plant weight by at least 70% compared to a substantially identical population of untreated plants. In some embodiments, administration of composition may increase the production plant weight by at least 80% compared to a substantially identical population of untreated plants. In some embodiments, administration of composition may increase the production plant weight by at least 90% compared to a substantially identical population of untreated plants. In some embodiments, administration of composition may increase the production plant weight by at least 100% compared to a substantially identical population of untreated plants. In some embodiments, administration of composition may increase the production plant weight by at least 110% compared to a substantially identical population of untreated plants.

In some embodiments, the administration of the composition may increase production fruit weight by 70-110% compared to a substantially identical population of untreated plants. In some embodiments, administration of composition may increase production fruit weight by at least 70% compared to a substantially identical population of untreated plants. In some embodiments, administration of composition may increase the production fruit weight by at least 80% compared to a substantially identical population of untreated plants. In some embodiments, administration of composition may increase the production fruit weight by at least 90% compared to a substantially identical population of untreated plants. In some embodiments, administration of composition may increase the production fruit weight by at least 100% compared to a substantially identical population of untreated plants. In some embodiments, administration of composition may increase the production fruit weight by at least 105% compared to a substantially identical population of untreated plants.

In some embodiments, the administration of the composition may increase the whole plant weight by 10-50% compared to a substantially identical population of untreated plants. In some embodiments, administration of the composition may increase the whole plant weight by at least 10% compared to a substantially identical population of untreated plants. In some embodiments, administration of the composition may increase the whole plant weight by at least 20% compared to a substantially identical population of untreated plants. In some embodiments, administration of the composition may increase the whole plant weight by at least 30% compared to a substantially identical population of untreated plants. In some embodiments, administration of the composition may increase the whole plant weight by at least 40% compared to a substantially identical population of untreated plants. In some embodiments, administration of the composition may increase the whole plant weight by at least 50% compared to a substantially identical population of untreated plants.

Seed Soak Application

In one non-limiting embodiment, the administration of the liquid composition may comprise soaking the seed in an effective amount of the liquid composition before planting the seed. In some embodiments, the administration of the liquid composition further comprises removing the seed from the liquid composition after soaking, and drying the seed before planting. In some embodiments, the seed may be soaked in the liquid composition for a time period in the range of 90-150 minutes. In some embodiments, the seed may be soaked in the liquid composition for a time period in the range of 110-130 minutes. In some embodiments, the seed may be soaked in the liquid composition for a time period in the range of 90-100 minutes. In some embodiments, the seed may be soaked in the liquid composition for a time period in the range of 100-110 minutes. In some embodiments, the seed may be soaked in the liquid composition for a time period in the range of 110-120 minutes. In some embodiments, the seed may be soaked in the liquid composition for a time period in the range of 120-130 minutes. In some embodiments, the seed may be soaked in the liquid composition for a time period in the range of 130-140 minutes. In some embodiments, the seed may be soaked in the liquid composition for a time period in the range of 140-150 minutes.

The composition may be diluted to a lower concentration for an effective amount in a seed soak application by mixing a volume of the composition in a volume of water. The percent solids of microalgae cells resulting in the diluted composition may be calculated by the multiplying the original percent solids in the composition by the ratio of the volume of the composition to the volume of water. Alternatively, the grams of microalgae cells in the diluted composition can be calculated by the multiplying the original grams of microalgae cells per 100 mL by the ratio of the volume of the composition to the volume of water. In some embodiments, the effective amount in a seed soak application of the liquid composition may comprise a concentration in the range of 6-10 mL/gallon, resulting in a reduction of the percent solids of microalgae cells from 5-30% to 0.007925-0.079252% (i.e., about 0.008% to about 0.080%, or about 0.008 g/100 mL to about 0.080 g/100 mL). In some embodiments, the effective amount in a seed soak application of the liquid composition may comprise a concentration in the range of 7-9 mL/gallon, resulting in a reduction of the percent solids of microalgae cells from 5-30% to 0.009245-0.071327% (i.e., about 0.009% to about 0.070%, or about 0.009 g/100 mL to about 0.070 g/100 mL). In some embodiments, the effective amount in a seed soak application of the liquid composition may comprise a concentration in the range of 6-7 mL/gallon, resulting in a reduction of the percent solids of microalgae cells from 5-30% to 0.007925-0.055476% (i.e., about 0.008% to about 0.055%, or about 0.008 g/100 mL to about 0.055 g/100 mL). In some embodiments, the effective amount in a seed soak application of the liquid composition may comprise a concentration in the range of 7-8 mL/gallon, resulting in a reduction of the percent solids of microalgae cells from 5-30% to 0.009246-0.063401% (i.e., about 0.009% to about 0.065%, or about 0.009 g/100 mL to about 0.065 g/100 mL). In some embodiments, the effective amount in a seed soak application of the liquid composition may comprise a concentration in the range of 8-9 mL/gallon, resulting in a reduction of the percent solids of microalgae cells from 5-30% to 0.010567-0.071327% (i.e., about 0.010% to about 0.070%, or about 0.010 g/100 mL). In some embodiments, the effective amount in a seed soak application of the liquid composition may comprise a concentration in the range of 9-10 mL/gallon, resulting in a reduction of the percent solids of microalgae cells from 5-30% to 0.011888-0.079252% (i.e., about 0.012% to about 0.080%, or about 0.012 g/100 mL to about 0.080 g/100 mL).

Soil Application—Seed

In another non-limiting embodiment, the administration of the composition may comprise contacting the soil in the immediate vicinity of the planted seed with an effective amount of the composition. In some embodiments, the liquid composition may be supplied to the soil by injection into a low volume irrigation system, such as but not limited to a drip irrigation system supplying water beneath the soil through perforated conduits or at the soil level by fluid conduits hanging above the ground or protruding from the ground. In some embodiments, the liquid composition may be supplied to the soil by a soil drench method wherein the liquid composition is poured on the soil.

The composition may be diluted to a lower concentration for an effective amount in a soil application by mixing a volume of the composition in a volume of water. The percent solids of microalgae cells resulting in the diluted composition may be calculated by the multiplying the original percent solids in the composition by the ratio of the volume of the composition to the volume of water. Alternatively, the grams of microalgae cells in the diluted composition can be calculated by the multiplying the original grams of microalgae cells per 100 mL by the ratio of the volume of the composition to the volume of water. In some embodiments, the effective amount in a soil application of the liquid composition may comprise a concentration in the range of 3.5-10 mL/gallon, resulting in a reduction of the percent solids of microalgae cells from 5-30% to 0.004623-0.079252% (i.e., about 0.004% to about 0.080%, or about 0.004 g/100 mL to about 0.080 g/100 mL). In some embodiments, the effective amount in a soil application of the liquid composition may comprise a concentration in the range of 3.5-4 mL/gallon, resulting in a reduction of the percent solids of microalgae cells from 5-30% to 0.004623-0.031701% (i.e., about 0.004% to about 0.032%, or about 0.004 g/100 mL to about 0.032 g/100 mL). In some embodiments, the effective amount in a soil application of the liquid composition may comprise a concentration in the range of 4-5 mL/gallon, resulting in a reduction of the percent solids of microalgae cells from 5-30% to 0.005283-0.039626% (i.e., about 0.005% to about 0.040%, or about 0.005 g/100 mL to about 0.040 g/100 mL). In some embodiments, the effective amount in a soil application of the liquid composition may comprise a concentration in the range of 5-6 mL/gallon, resulting in a reduction of the percent solids of microalgae cells from 5-30% to 0.006604-0.047551% (i.e., about 0.006% to about 0.050%, or about 0.006 g/100 ml to about 0.050 g/100 mL). In some embodiments, the effective amount in a soil application of the liquid composition may comprise a concentration in the range of 6-7 mL/gallon, resulting in a reduction of the percent solids of microalgae cells from 5-30% to 0.007925-0.055476% (i.e., about 0.008% to about 0.055%, or about 0.008 g/100 mL to about 0.055 g/100 mL). In some embodiments, the effective amount in a soil application of the liquid composition may comprise a concentration in the range of 7-8 mL/gallon, resulting in a reduction of the percent solids of microalgae cells from 5-30% to 0.009246-0.063401% (i.e., about 0.009% to about 0.065%, or about 0.009 g/100 mL to about 0.065 g/100 mL). In some embodiments, the effective amount in a soil application of the liquid composition may comprise a concentration in the range of 8-9 mL/gallon, resulting in a reduction of the percent solids of microalgae cells from 5-30% to 0.010567-0.071327% (i.e., about 0.010% to about 0.075%, or about 0.010 g/100 mL to about 0.075 g/100 mL). In some embodiments, the effective amount in a soil application of the liquid composition may comprise a concentration in the range of 9-10 mL/gallon, resulting in a reduction of the percent solids of microalgae cells from 5-30% to 0.011888-0.079252% (i.e., about 0.012% to about 0.080%, or about 0.012 g/100 mL to about 0.080 g/100 mL).

The rate of application of the composition at the desired concentration may be expressed as a volume per area. In some embodiments, the rate of application of the liquid composition in a soil application may comprise a rate in the range of 50-150 gallons/acre. In some embodiments, the rate of application of the liquid composition in a soil application may comprise a rate in the range of 75-125 gallons/acre. In some embodiments, the rate of application of the liquid composition in a soil application may comprise a rate in the range of 50-75 gallons/acre. In some embodiments, the rate of application of the liquid composition in a soil application may comprise a rate in the range of 75-100 gallons/acre. In some embodiments, the rate of application of the liquid composition in a soil application may comprise a rate in the range of 100-125 gallons/acre. In some embodiments, the rate of application of the liquid composition in a soil application may comprise a rate in the range of 125-150 gallons/acre.

Capillary Action Application

In another non-limiting embodiment, the administration of the liquid composition may comprise first soaking the seed in water, removing the seed from the water, drying the seed, applying an effective amount of the liquid composition below the seed planting level in the soil, and planting the seed, wherein the liquid composition supplied to the seed from below by capillary action. In some embodiments, the seed may be soaked in water for a time period in the range of 90-150 minutes. In some embodiments, the seed may be soaked in water for a time period in the range of 110-130 minutes. In some embodiments, the seed may be soaked in water for a time period in the range of 90-100 minutes. In some embodiments, the seed may be soaked in water for a time period in the range of 100-110 minutes. In some embodiments, the seed may be soaked in water for a time period in the range of 110-120 minutes. In some embodiments, the seed may be soaked in water for a time period in the range of 120-130 minutes. In some embodiments, the seed may be soaked in water for a time period in the range of 130-140 minutes. In some embodiments, the seed may be soaked in water for a time period in the range of 140-150 minutes.

The composition may be diluted to a lower concentration for an effective amount in a capillary action application by mixing a volume of the composition in a volume of water. The percent solids of microalgae cells resulting in the diluted composition may be calculated by the multiplying the original percent solids in the composition by the ratio of the volume of the composition to the volume of water. Alternatively, the grams of microalgae cells in the diluted composition can be calculated by the multiplying the original grams of microalgae cells per 100 mL by the ratio of the volume of the composition to the volume of water. In some embodiments, the effective amount in a capillary action application of the liquid composition may comprise a concentration in the range of 6-10 mL/gallon, resulting in a reduction of the percent solids of microalgae cells from 5-30% to 0.007925-0.079252% (i.e., about 0.008% to about 0.080%, or about 0.008 g/100 mL to about 0.080 g/100 mL). In some embodiments, the effective amount in a capillary action application of the liquid composition may comprise a concentration in the range of 7-9 mL/gallon, resulting in a reduction of the percent solids of microalgae cells from 5-30% to 0.009245-0.071327% (i.e., about 0.009% to about 0.075%, or about 0.009 g/100 mL to about 0.075 g/100 mL). In some embodiments, the effective amount in a capillary action application of the liquid composition may comprise a concentration in the range of 6-7 mL/gallon, resulting in a reduction of the percent solids of microalgae cells from 5-30% to 0.007925-0.05547% (i.e., about 0.008% to about 0.055%, or about 0.008 g/100 mL to about 0.055 g/100 mL). In some embodiments, the effective amount in a capillary action application of the liquid composition may comprise a concentration in the range of 7-8 mL/gallon, resulting in a reduction of the percent solids of microalgae cells from 5-30% to 0.009246-0.063401% (i.e., about 0.009% to about 0.065%, or about 0.009 g/100 mL to about 0.065 g/100 mL). In some embodiments, the effective amount in a capillary action application of the liquid composition may comprise a concentration in the range of 8-9 mL/gallon, resulting in a reduction of the percent solids of microalgae cells from 5-30% to 0.010567-0.071327% (i.e., about 0.010% to about 0.075%, or about 0.010 g/100 mL to about 0.075 g/100 mL). In some embodiments, the effective amount in a capillary action application of the liquid composition may comprise a concentration in the range of 9-10 mL/gallon, resulting in a reduction of the percent solids of microalgae cells from 5-30% to 0.011888-0.079252% (i.e., about 0.012% to about 0.080%, or about 0.012 g/100 mL to about 0.080 g/100 mL).

Hydroponic Application

In another non-limiting embodiment, the administration of the liquid composition to a seed or plant may comprise applying the microalga based composition in combination with a nutrient medium to seeds disposed in and plants growing in a hydroponic growth medium or an inert growth medium (e.g., coconut husks). The liquid composition may be applied multiple times per day, per week, or per growing season.

Foliar Application

In one non-limiting embodiment, the administration of the composition may comprise contacting the foliage of the plant with an effective amount of the composition. In some embodiments, the liquid composition may be sprayed on the foliage by a hand sprayer, a sprayer on an agriculture implement, or a sprinkler.

The composition may be diluted to a lower concentration for an effective amount in a foliar application by mixing a volume of the composition in a volume of water. The percent solids of microalgae cells resulting in the diluted composition may be calculated by the multiplying the original percent solids in the composition by the ratio of the volume of the composition to the volume of water. Alternatively, the grams of microalgae cells in the diluted composition can be calculated by the multiplying the original grams of microalgae cells per 100 mL by the ratio of the volume of the composition to the volume of water. In some embodiments, the effective amount in a foliar application of the liquid composition may comprise a concentration in the range of 2-10 mL/gallon, resulting in a reduction of the percent solids of microalgae cells from 5-30% to 0.002642-0.079252% (i.e., about 0.003% to about 0.080%, or about 0.003 g/100 mL to about 0.080 g/100 mL). In some embodiments, the effective amount in a foliar application of the liquid composition may comprise a concentration in the range of 2-3 mL/gallon, resulting in a reduction of the percent solids of microalgae cells from 5-30% to 0.002642-0.023775% (i.e., about 0.003% to about 0.025%, or about 0.003 g/100 mL to about 0.025 g/100 mL). In some embodiments, the effective amount in a foliar application of the liquid composition may comprise a concentration in the range of 3-4 mL/gallon, resulting in a reduction of the percent solids of microalgae cells from 5-30% to 0.003963-0.031701% (i.e., about 0.004% to about 0.035%, or about 0.004 g/100 mL to about 0.035 g/100 mL). In some embodiments, the effective amount in a foliar application of the liquid composition may comprise a concentration in the range of 4-5 mL/gallon, resulting in a reduction of the percent solids of microalgae cells from 5-30% to 0.005283-0.039626% (i.e., about 0.005% to about 0.040%, or about 0.005 g/100 mL to about 0.040 g/100 mL). In some embodiments, the effective amount in a foliar application of the liquid composition may comprise a concentration in the range of 5-6 mL/gallon, resulting in a reduction of the percent solids of microalgae cells from 5-30% to 0.006604-0.047551% (i.e., about 0.007% to about 0.050%, or about 0.007 g/100 mL to about 0.050 g/100 mL). In some embodiments, the effective amount in a foliar application of the liquid composition may comprise a concentration in the range of 6-7 mL/gallon, resulting in a reduction of the percent solids of microalgae cells from 5-30% to 0.007925-0.055476% (i.e., about 0.008% to about 0.055%, or about 0.008 g/100 mL to about 0.055 g/100 mL). In some embodiments, the effective amount in a foliar application of the liquid composition may comprise a concentration in the range of 7-8 mL/gallon, resulting in a reduction of the percent solids of microalgae cells from 5-30% to 0.009246-0.063401% (i.e., about 0.009% to about 0.065%, or about 0.009 g/100 mL to about 0.065 g/100 mL). In some embodiments, the effective amount in a foliar application of the liquid composition may comprise a concentration in the range of 8-9 mL/gallon, resulting in a reduction of the percent solids of microalgae cells from 5-30% to 0.010567-0.071327% (i.e., about 0.010% to about 0.070%, or about 0.010 g/100 mL to about 0.070 g/100 mL). In some embodiments, the effective amount in a foliar application of the liquid composition may comprise a concentration in the range of 9-10 mL/gallon, resulting in a reduction of the percent solids of microalgae cells from 5-30% to 0.011888-0.079252% (i.e., about 0.012% to about 0.080%, or about 0.012 g/100 mL to about 0.080 g/100 mL).

The rate of application of the composition at the desired concentration may be expressed as a volume per area. In some embodiments, the rate of application of the liquid composition in a foliar application may comprise a rate in the range of 10-50 gallons/acre. In some embodiments, the rate of application of the liquid composition in a foliar application may comprise a rate in the range of 10-15 gallons/acre. In some embodiments, the rate of application of the liquid composition in a foliar application may comprise a rate in the range of 15-20 gallons/acre. In some embodiments, the rate of application of the liquid composition in a foliar application may comprise a rate in the range of 20-25 gallons/acre. In some embodiments, the rate of application of the liquid composition in a foliar application may comprise a rate in the range of 25-30 gallons/acre. In some embodiments, the rate of application of the liquid composition in a foliar application may comprise a rate in the range of 30-35 gallons/acre. In some embodiments, the rate of application of the liquid composition in a foliar application may comprise a rate in the range of 35-40 gallons/acre. In some embodiments, the rate of application of the liquid composition in a foliar application may comprise a rate in the range of 40-45 gallons/acre. In some embodiments, the rate of application of the liquid composition in a foliar application may comprise a rate in the range of 45-50 gallons/acre.

The frequency of the application of the composition may be expressed as the number of applications per period of time (e.g., two applications per month), or by the period of time between applications (e.g., one application every 21 days). In some embodiments, the plant may be contacted by the composition in a foliar application every 3-28 days. In some embodiments, the plant may be contacted by the composition in a foliar application every 4-10 days. In some embodiments, the plant may be contacted by the composition in a foliar application every 18-24 days. In some embodiments, the plant may be contacted by the composition in a foliar application every 3-7 days. In some embodiments, the plant may be contacted by the composition in a foliar application every 7-14 days. In some embodiments, the plant may be contacted by the composition in a foliar application every 14-21 days. In some embodiments, the plant may be contacted by the composition in a foliar application every 21-28 days.

Foliar application(s) of the composition generally begin after the plant has become established, but may begin before establishment, at defined time period after planting, or at a defined time period after emergence form the soil in some embodiments. In some embodiments, the plant may be first contacted by the composition in a foliar application 5-14 days after the plant emerges from the soil. In some embodiments, the plant may be first contacted by the composition in a foliar application 5-7 days after the plant emerges from the soil. In some embodiments, the plant may be first contacted by the composition in a foliar application 7-10 days after the plant emerges from the soil. In some embodiments, the plant may be first contacted by the composition in a foliar application 10-12 days after the plant emerges from the soil. In some embodiments, the plant may be first contacted by the composition in a foliar application 12-14 days after the plant emerges from the soil.

Soil Application—Plant

In another non-limiting embodiment, the administration of the composition may comprise contacting the soil in the immediate vicinity of the plant with an effective amount of the composition. In some embodiments, the liquid composition may be supplied to the soil by injection into to a low volume irrigation system, such as but not limited to a drip irrigation system supplying water beneath the soil through perforated conduits or at the soil level by fluid conduits hanging above the ground or protruding from the ground. In some embodiments, the liquid composition may be supplied to the soil by a soil drench method wherein the liquid composition is poured on the soil.

The composition may be diluted to a lower concentration for an effective amount in a soil application by mixing a volume of the composition in a volume of water. The percent solids of microalgae cells resulting in the diluted composition may be calculated by the multiplying the original percent solids of microalgae cells in the composition by the ratio of the volume of the composition to the volume of water. Alternatively, the grams of microalgae cells in the diluted composition can be calculated by the multiplying the original grams of microalgae cells per 100 mL by the ratio of the volume of the composition to the volume of water. In some embodiments, the effective amount in a soil application of the liquid composition may comprise a concentration in the range of 1-50 mL/gallon, resulting in a reduction of the percent solids of microalgae cells from 5-30% to 0.001321-0.396258% (i.e., about 0.001% to about 0.400%, or about 0.001 g/100 mL to about 0.400 g/100 mL). In some embodiments, the effective amount in a soil application of the liquid composition may comprise a concentration in the range of 1-10 mL/gallon, resulting in a reduction of the percent solids of microalgae cells from 5-30% to 0.001321-0.079252% (i.e., about 0.001% to about 0.080%, or about 0.001 g/100 mL to about 0.080 g/100 mL). In some embodiments, the effective amount in a soil application of the liquid composition may comprise a concentration in the range of 2-7 mL/gallon, resulting in a reduction of the percent solids of microalgae cells from 5-30% to 0.002642-0.055476% (i.e., about 0.003% to about 0.055%, or about 0.003 g/100 mL to about 0.055 g/100 mL). In some embodiments, the effective amount in a soil application of the liquid composition may comprise a concentration in the range of 10-20 mL/gallon, resulting in a reduction of the percent solids of microalgae cells from 5-30% to 0.013201-0.158503% (i.e., about 0.013% to about 0.160%, or about 0.013 g/100 mL to about 0.160 g/100 mL). In some embodiments, the effective amount in a soil application of the liquid composition may comprise a concentration in the range of 20-30 mL/gallon, resulting in a reduction of the percent solids of microalgae cells from 5-30% to 0.026417-0.237755% (i.e., about 0.025% to about 0.250%, or about 0.025 g/100 mL to about 0.250 g/100 mL). In some embodiments, the effective amount in a soil application of the liquid composition may comprise a concentration in the range of 30-45 mL/gallon, resulting in a reduction of the percent solids of microalgae cells from 5-30% to 0.039626-0.356631% (i.e., about 0.040% to about 0.360%, or about 0.040 g/100 mL to about 0.360 g/100 mL). In some embodiments, the effective amount in a soil application of the liquid composition may comprise a concentration in the range of 30-40 mL/gallon, resulting in a reduction of the percent solids of microalgae cells from 5-30% to 0.039626-0.317007% (i.e., about 0.040% to about 0.320%, or about 0.040 g/100 mL to about 0.320 g/100 mL). In some embodiments, the effective amount in a soil application of the liquid composition may comprise a concentration in the range of 40-50 mL/gallon, resulting in a reduction of the percent solids of microalgae cells from 5-30% to 0.052834-0.396258% (i.e., about 0.055% to about 0.400%, or about 0.055 g/100 mL to about 0.400 g/100 mL).

The rate of application of the composition at the desired concentration may be expressed as a volume per area. In some embodiments, the rate of application of the liquid composition in a soil application may comprise a rate in the range of 50-150 gallons/acre. In some embodiments, the rate of application of the liquid composition in a soil application may comprise a rate in the range of 75-125 gallons/acre. In some embodiments, the rate of application of the liquid composition in a soil application may comprise a rate in the range of 50-75 gallons/acre. In some embodiments, the rate of application of the liquid composition in a soil application may comprise a rate in the range of 75-100 gallons/acre. In some embodiments, the rate of application of the liquid composition in a soil application may comprise a rate in the range of 100-125 gallons/acre. In some embodiments, the rate of application of the liquid composition in a soil application may comprise a rate in the range of 125-150 gallons/acre.

The frequency of the application of the composition may be expressed as the number of applications per period of time (e.g., two applications per month), or by the period of time between applications (e.g., one application every 21 days). In some embodiments, the plant may be contacted by the composition in a soil application every 3-28 days. In some embodiments, the plant may be contacted by the composition in a soil application every 4-10 days. In some embodiments, the plant may be contacted by the liquid composition in a soil application every 18-24 days. In some embodiments, the plant may be contacted by the composition in a soil application every 3-7 days. In some embodiments, the plant may be contacted by the composition in a soil application every 7-14 days. In some embodiments, the plant may be contacted by the composition in a soil application every 14-21 days. In some embodiments, the plant may be contacted by the composition in a soil application every 21-28 days.

Soil application(s) of the composition generally begin after the plant has become established, but may begin before establishment, at defined time period after planting, or at a defined time period after emergence form the soil in some embodiments. In some embodiments, the plant may be first contacted by the composition in a soil application 5-14 days after the plant emerges from the soil. In some embodiments, the plant may be first contacted by the composition in a soil application 5-7 days after the plant emerges from the soil. In some embodiments, the plant may be first contacted by the liquid composition in a soil application 7-10 days after the plant emerges from the soil. In some embodiments, the plant may be first contacted by the composition in a soil application 10-12 days after the plant emerges from the soil. In some embodiments, the plant may be first contacted by the composition in a soil application 12-14 days after the plant emerges from the soil.

Whether in a seed soak, soil, capillary action, foliar, or hydroponic application the method of use comprises relatively low concentrations of the composition. Even at such low concentrations, the described composition has been shown to be effective at producing an enhanced characteristic in plants. The ability to use low concentrations allows for a reduced impact on the environment that may result from over application and an increased efficiency in the method of use of the composition by requiring a small amount of material to produce the desired effect. In some embodiments, the use of the liquid composition with a low volume irrigation system in soil applications allows the low concentration of the liquid composition to remain effective and not be diluted to a point where the composition is no longer in at a concentration capable of producing the desired effect on the plants while also increasing the grower's water use efficiency.

In conjunction with the low concentrations of microalgae cells in the composition necessary to be effective for enhancing the described characteristics of plants, the composition may does not have be to administered continuously or at a high frequency (e.g., multiple times per day, daily). The ability of the composition to be effective at low concentrations and a low frequency of application was an unexpected result, due to the traditional thinking that as the concentration of active ingredients decreases the frequency of application should increase to provide adequate amounts of the active ingredients. Effectiveness at low concentration and application frequency increases the material usage efficiency of the method of using the composition while also increasing the yield efficiency of the agricultural process.

Administration of a dried microalgae composition treatment to the soil, seed, or plant can be in an amount effective to produce an enhanced characteristic in the plant compared to a substantially identical population of untreated plant. Such enhanced characteristics can comprise accelerated seed germination, accelerated seedling emergence, improved seedling emergence, improved leaf formation, accelerated leaf formation, improved plant maturation, accelerated plant maturation, increased plant yield, increased plant growth, increased plant quality, increased plant health, increased flowering, increased fruit yield, increased fruit growth, and increased fruit quality. Non-limiting examples of such enhanced characteristics can comprise accelerated achievement of the hypocotyl stage, accelerated protrusion of a stem from the soil, accelerated achievement of the cotyledon stage, accelerated leaf formation, increased leaf size, increased leaf area index, increased marketable plant weight, increased marketable plant yield, increased marketable fruit weight, increased production plant weight, increased production fruit weight, increased utilization (indicator of efficiency in the agricultural process based on ratio of marketable fruit to unmarketable fruit), increased chlorophyll content (indicator of plant health), increased plant weight (indicator of plant health), increased root weight (indicator of plant health), increased root mass (indicator of plant health), increased shoot weight (indicator of plant health), increased plant height, increased thatch height, increased resistance to salt stress, increased plant resistance to heat stress, increased plant resistance to heavy metal stress, increased plant resistance to drought, improved color, reduced insect damage, reduced blossom end rot, and reduced sun burn. Such enhanced characteristics can occur individually in a plant, or in combinations of multiple enhanced characteristics. The characteristic of flowering has is important for not only the ornamental market, but also for fruiting plants where an increase in flowering may correlate to an increase in fruit production.

Seed Coating

In one non-limiting embodiment, the administration of the dried microalgae composition treatment can comprise coating a seed. In some embodiments, a seed may be coated by passing through a slurry comprising microalgae and then dried. In some embodiments, the seed may be coated with the dried microalgae composition and other components such as, but not limited to, binders and fillers known in the art to be suitable for coating seeds. The fillers may comprise suitable inorganic particles such as, but not limited to, silicate particles, carbonate particles, and sulphate particles, quartz, zeolites, pumice, perlite, diatomaceous earth, pyrogene silica, $Sb_2O_3$, $TiO_2$, lithopone, ZnO, and hydrated aluminum oxide. The binders may include, but are not limited to, water-soluble polymers, polyvinyl acetate, polyvinyl alcohol, polyvinyl pyrrolidone, polyurethane, methyl cellulose, carboxymethyl cellulose, hydroxylpropyl cellulose, sodium alginate, polyacrylate, casein, gelatin, pullulan, polyacrylamide, polyethylene oxide, polystyrene, styrene acrylic copolymers, styrene butadiene polymers, poly (N-vinylacetamide), waxes, carnauba wax, paraffin wax, polyethylene wax, bees wax, polypropylene wax, and ethylene vinyl acetate. In some embodiments, the seed coating may comprise a wetting and dispersing additive such as, but not limited to polyacrylates, organo-modified polyacrylates, sodium polyacrylates, polyurethanes, phosphoric acid esters, star polymers, and modified polyethers.

In some embodiments, the seed coating may comprise other components such as, but not limited to, a solvent, thickener, colouring agent, anti-foaming agent, biocide, surfactant, and pigment. In some embodiments, the seed coating may comprise a hydrogel or film coating materials. In some embodiments, the concentration of dried microalgae in the seed coating may comprise 0.1-20% solids. In some embodiments, the concentration of microalgae in the seed coating may comprise less than 0.1% solids. In some embodiments, the concentration of dried microalgae in the seed coating may comprise 0.1-1% solids. In some embodiments, the concentration of dried microalgae in the seed coating may comprise 1-2% solids. In some embodiments, the concentration of dried microalgae in the seed coating may comprise 2-3% solids. In some embodiments, the concentration of dried microalgae in the seed coating may comprise 3-5% solids. In some embodiments, the concentration of dried microalgae in the seed coating may comprise 5-10% solids. In some embodiments, the concentration of dried microalgae in the seed coating may comprise 10-15% solids. In some embodiments, the concentration of dried microalgae in the seed coating may comprise 15-20% solids.

In some embodiments, the seed may be coated in single step. In some embodiments, the seed may be coated in multiple steps. Conventional or otherwise suitable coating equipment or techniques may be used to coat the seeds. Suitable equipment may include drum coaters, fluidized beds, rotary coaters, side vended pan, tumble mixers, and spouted beds. Suitable techniques may comprise mixing in a container, tumbling, spraying, or immersion. After coating, the seeds may be dried or partially dried.

Soil Application

In another non-limiting embodiment, the administration of the dried microalgae composition treatment can comprise mixing an effective amount of the composition with a solid growth medium, such as soil, potting mix, compost, or inert hydroponic material, prior to planting a seed, seedling, or plant in the solid growth medium. The dried microalgae composition may be mixed in the solid growth medium at an inclusion level of 0.1-20% by volume. In some embodiments, the effective amount in a mixed solid growth medium application of the dried microalgae composition can comprise a concentration in the range of 0.1-1% solids. In some embodiments, the effective amount in a mixed solid growth medium application of the dried microalgae composition can comprise a concentration in the range of 1-3%% solids. In some embodiments, the effective amount in a mixed solid growth medium application of the dried microalgae composition can comprise a concentration in the range of 3-5% solids. In some embodiments, the effective amount in a mixed solid growth medium application of the dried microalgae composition can comprise a concentration in the range of 5-10% solids. In some embodiments, the effective amount in a mixed solid growth medium application of the dried microalgae composition can comprise a concentration in the range of 10-20% solids.

In another non-limiting embodiment, the administration of the dried microalgae composition treatment can comprise inclusion in a solid growth medium during in-furrow plants or broadcast application to the ground. The dried microalgae composition may be applied at an rate of 50-500 grams/acre. In some embodiments, the application rate of the dried microalgae composition can comprise 50-100 grams/acre. In some embodiments, the application rate of the dried microalgae composition can comprise 100-150 grams/acre. In some embodiments, the application rate of the dried microalgae composition can comprise 150-200 grams/acre. In some embodiments, the application rate of the dried microalgae composition can comprise 200-250 grams/acre. In some embodiments, the application rate of the dried microalgae composition can comprise 250-300 grams/acre. In some embodiments, the application rate of the dried microalgae composition can comprise 300-350 grams/acre. In some embodiments, the application rate of the dried microalgae composition can comprise 350-400 grams/acre. In some embodiments, the application rate of the dried microalgae composition can comprise 400-450 grams/acre. In some embodiments, the application rate of the dried microalgae composition can comprise 450-500 grams/acre.

EXAMPLES

Embodiments of the invention are exemplified and additional embodiments are disclosed in further detail in the following Examples, which are not in any way intended to limit the scope of any aspect of the invention described herein.

Example 1

An experiment was conducted to determine if application of a low concentration of a *Haematococcus* based composition to tomato seeds planted in soil affected the rate at which the seedlings emerge from the soil. Tomatoes are part of the Solanaceae family. Tomato seeds (*Solanum lycopersicum*) were planted in trays with standard soilless plant potting soil mix. Ten treatments were compared to an untreated control (UTC) and are listed in Table 2. The *Haematococcus pluvialis* extracted biomass was mechanically lysed before being subjected to a supercritical carbon dioxide extraction process. A commercially available macroalgae extract based product was obtained from Acadian Seaplants Limited (30 Brown Avenue, Dartmouth, Nova Scotia, Canada, B3B 1X8) for comparison. The commercially available product Transit Soil from FBSciences, Inc. (153 N Main Street, Ste 100, Collierville, Tenn. 38017) was also tested.

TABLE 2

| Treatment No. | Treatment Description |
| --- | --- |
| 1 | UTC - untreated water check |
| 2 | Phototrophic *Haematococcus pluvialis* - Extracted Biomass |
| 3 | Phototrophic *Haematococcus pluvialis* extracted biomass plus *Kappaphycus* liquid extract |
| 4 | Grower Standard Product - Acadian Liquid Seaweed Concentrate |
| 5 | Grower Standard Product - Transit Soil |

The treatments were pasteurized, normalized to 10% solids (for treatments with microalgal solids), and stabilized with phosphoric acid ($H_3PO_4$) and potassium sorbate ($C_6H_7KO_2$), with the remaining balance consisting of water. The *Kappaphycus* liquid extract comprises 10% by volume of the liquid composition.

All treatments were applied to the seeds at the low concentration of 4.73 mL/gallon. The treatment method consisted of drenching the soil at a rate of 100 gallons/acre using a watering can. The treatments were applied immediately after planting the seeds. The tested concentration of 4.73 mL/gallon diluted the composition which originally contained 10% solids by weight of *Haematococcus* cells to the low percent solids content of only 0.012495% (or about 0.012495 g of microalgae cells/100 mL of water).

Each treatment was applied to 100 seeds planted in a 10 by 10 pattern in planting trays, with each row of ten counting as a replicate (10 total replicates). Visual observations were made daily to record the percentage of plants that have emerged from the soil. The standard used for assessing emergence was the hypocotyl stage where a stem was visible to be protruding from the potting soil mix. The experiment was conducted inside a greenhouse with all seeds and treatments subjected to the same controlled conditions including temperature and light. All trays were treated with the same amount of water throughout the experiment. No additional nutrients were provided to the plants during the experiment. All data rated as significant was done so utilizing the New Duncan's Multiple Test Range at a 90% confidence level, such that values with a statistical significant identifier of the same letter are not significantly different.

Results are shown in Tables 3-6 with accompanying statistical significance grouping identifiers.

TABLE 3

| | Plant Emergence (Ave. % of plants emerged on date) | | | | | | | | | | | |
|---|---|---|---|---|---|---|---|---|---|---|---|---|
| | Day 1 | | | | Day 2 | | | | Day 3 | | | |
| | AM | | PM | | AM | | PM | | AM | | PM | |
| 1 | 0 | a | 0 | c | 0 | d | 2 | f | 3 | d | 16 | d |
| 2 | 0 | a | 3 | c | 4 | c | 24 | d | 26 | bcd | 60 | b |
| 3 | 0 | a | 6 | b | 7 | bc | 33 | c | 36 | bc | 58 | b |
| 4 | 0 | a | 0 | c | 0 | d | 18 | de | 19 | cd | 6 | b |
| 5 | 0 | a | 0 | c | 0 | d | 16 | de | 44 | ab | 44 | c |

TABLE 4

| | Plant Emergence (Ave. % of plants emerged on date) | | | | | | | | | | | |
|---|---|---|---|---|---|---|---|---|---|---|---|---|
| | Day 4 | | | | Day 5 | | | | Day 6 | | Day 7 | |
| | AM | | PM | | AM | | PM | | PM | | PM | |
| 1 | 17 | g | 47 | g | 55 | e | 76 | a | 83 | a | 84 | a |
| 2 | 61 | bcd | 73 | a-e | 79 | abc | 84 | a | 84 | a | 85 | a |
| 3 | 62 | bcd | 75 | a-d | 76 | a-d | 76 | a | 80 | a | 81 | a |
| 4 | 62 | bcd | 79 | abc | 79 | abc | 85 | a | 89 | a | 88 | a |
| 5 | 47 | ef | 68 | cde | 72 | a-d | 79 | a | 83 | a | 84 | a |

As shown in Tables 3-4, treatments 2 and 3 comprising the *Haematococcus* based compositions emerged out of the soil sooner than the UTC, showing a statistically significance difference on Days 2, 3 (PM), 4, and 5 (AM). The percentage of plants emerged for all treatments converged at the end of the experiment.

TABLE 5

| | Plant Emergence (Ave. % of plants emerged at observation time) | | | | | | | | | |
|---|---|---|---|---|---|---|---|---|---|---|
| | Untreated Water Check (UTC) | | Phototrophic *Haematococcus pluvialis* - Extracted Biomass (Treatment 2) | | % Increase over UTC | | Phototrophic *Haematococcus pluvialis* extracted biomass plus *Kappaphycus* liquid extract (Treatment 3) | | % Increase over UTC | |
| Day 1 AM | 0 | a | 0 | a | | | 0 | a | | |
| Day 1 PM | 0 | c | 3 | c | | | 6 | b | | |
| Day 2 AM | 0 | d | 4 | c | | | 7 | bc | | |
| Day 2 PM | 2 | f | 24 | d | 1100% | | 33 | c | 1550% | |
| Day 3 AM | 3 | d | 26 | bcd | 767% | | 36 | bc | 1100% | |
| Day 3 PM | 16 | d | 60 | b | 275% | | 58 | b | 263% | |
| Day 4 AM | 17 | g | 61 | bcd | 259% | | 62 | bcd | 265% | |
| Day 4 PM | 47 | g | 73 | a-e | 55% | | 75 | a-d | 60% | |
| Day 5 AM | 55 | e | 79 | abc | 44% | | 76 | a-d | 38% | |
| Day 5 PM | 76 | a | 84 | a | 11% | | 76 | a | 0% | |
| Day 6 PM | 83 | a | 84 | a | 1% | | 80 | a | -3% | |
| Day 7 PM | 84 | a | 85 | a | 1% | | 81 | a | -4% | |

Table 5 shows treatments 2 and 2 comprising the *Haematococcus* based composition with respect to the UTC. As shown in Table 5, treatments 2 and 3 reached at least 70% emergence a day before the UTC, and maintained a numerical increase of at least 38% over the UTC through Day 5 AM.

TABLE 6

Plant Emergence (Ave. % of plants emerged on Day 4 AM)

| | 22-May AM | | % increase over UTC |
|---|---|---|---|
| UTC - untreated water check | 17 | f | |
| Phototrophic *Haematococcus pluvialis* - Extracted Biomass | 61 | bcd | 259% |
| Phototrophic *Haematococcus pluvialis* extracted biomass plus *Kappaphycus* liquid extract | 62 | abc | 265% |
| Grower Standard Product - Acadian Liquid Seaweed Concentrate | 62 | abc | 265% |
| Grower Standard Product - Transit Soil | 47 | de | 176% |

Table 6 displays the data from the Day 4 AM, and shows a statistically significant difference for the *Haematococcus* based composition as compared to the UTC, which amounts to a numerical increase of over 250%.

Example 2

An experiment was conducted to determine if a low concentration and low frequency application of a *Haematococcus* based composition to bell pepper plants by soil application affected the yield of the plants. Bell pepper (*Capsicum annuum*) are part of the Solanaceae plant family and seeds were planted in a field in Ventura County, Calif. Two treatments were compared to an untreated control (UTC) and are listed in Table 7. A commercially available macroalgae extract based product was obtained from Acadian Seaplants Limited (30 Brown Avenue, Dartmouth, Nova Scotia, Canada, B3B 1X8) for comparison.

TABLE 7

| Treatment No. | Treatment Description |
|---|---|
| 1 | UTC - untreated water check |
| 2 | Phototrophic *Haematococcus* extracted biomass plus *Kappaphycus* liquid extract |
| 3 | Grower Standard Product - Acadian Liquid Seaweed Concentrate |

The *Haematococcus* based composition was pasteurized, normalized to 10% solids and 10% volume of *Kappaphycus* liquid extract), and stabilized with phosphoric acid ($H_3PO_4$) and potassium sorbate ($C_6H_7KO_2$), with the remaining balance consisting of water.

The *Haematococcus* based composition was applied at a low concentration of 37.85 mL/gallon. The tested concentration of 37.85 mL/gallon diluted the composition which originally contained 10% solids by weight of *Haematococcus* cells to the low percent solids content of only 0.099989% (or 0.099989 g of microalgae cells/100 mL of water). The Acadian treatment was applied at a concentration of 18.9 mL/gallon. Five total treatments were applied at a low frequency (i.e., averaging about 20 days between applications), starting three weeks after plant establishment. The treatments occurred with 20 days between the first and second, 24 days between the second and third, 11 days between the third and fourth, and 26 days between the fourth and fifth. The low concentration and low frequency treatments were applied by injection into a low volume irrigation drip system supplying water at a rate of 100 gallons/acre using a Hypro pump operating at 25 psi.

The experiment was set up as a block designed study of eight replicates consisting of 30 seeds each. Visual observations were used to evaluate plant vigor on a scale of 0-5, with 0 corresponding to plant death and 5 corresponding to complete health. Production was evaluated by quality in the two categories of marketable and unmarketable. Unmarketable fruit was considered fruit which had heavy insect damage, blossom end rot, softness, and/or heavy sunburn. The field used in the experiment was growing bell peppers for processing, and thus the quality needed for fresh market produce was not the target achievement. Additionally, the bell peppers were left in the field a length of time to ensure the maximum amount of reddening before harvest for processing. The chlorophyll content was estimated by an SPAD value (Soil-Plant Analysis Development), a numeric value provided by a Minolta SPAD meter which analyzes the amount of light in a specific light spectrum passing through a leaf and converts that reading to a numerical value as an indicator of chlorophyll density in the leaf. Production was evaluated by sampling based on picking all fruit to be found on two plants and replicating this process eight times per treatment. All fruit was weighed, counted, and reported as grams total weight per two plants and grams total weight on average per fruit. All data rated as significant was done so utilizing the Least Significant Difference analysis at a 90% confidence level, such that values with a statistical significant identifier of the same letter are not significantly different. Results are shown in Tables 2-16 for the treatments designated with an S for soil application, along with accompanying statistical significance identifiers.

Example 3

An experiment was conducted to determine if a low concentration and low frequency application of *Haematococcus* based composition to bell pepper plants (*Capsicum annuum*) by foliar application affected the yield of the plants. The foliar trial occurred in the same location, with the same treatments, and with the same design as the experiment of Example 2.

The *Haematococcus* based composition was applied at a low concentration of 7 mL/gallon. The tested concentration of 7 mL/gallon diluted the composition which originally contained 10% solids by weight of *Haematococcus* cells to the low percent solids content of only 0.018492% (or 0.018492 g of microalgae cells/100 mL of water). The Acadian treatment was applied at a concentration of 18.9 mL/gallon. Five total treatments were applied at a low frequency (i.e., averaging about 21 days between applications), starting three weeks after plant establishment. The treatments occurred with 20 days between the first and second, 23 days between the second and third, 15 days between the third and fourth, and 27 days between the fourth and fifth. The low concentration and low frequency treatments were applied directly to the foliage at a rate of 25 gallons/acre with a backpack sprayer operating at 40 psi through a Hollow Co. nozzle size D-6.

All data rated as significant was done so utilizing the Least Significant Difference analysis at a 90% confidence level, such that values with a statistical significant identifier of the same letter are not significantly different. Results are shown in Tables 8-22 for the treatments designated with an F for foliar application, along with accompanying statistical significance identifiers. It was noted by the time the field was harvested many of the above mentioned unmarketable quality issues did occur and thus the ratio of unmarketable fruit was higher in this field than one might expect.

TABLE 8

Plant Sizing - Whole plant (grams) (A = early, B = later)

|   | | Avg. A | | Increase over UTC | Avg. B | | Increase over UTC |
|---|---|---|---|---|---|---|---|
| 1 | UTC - untreated water check F | 4.3 | a | | 31.2 | a | |
|   | UTC - untreated water check S | 4.4 | a | | 24.8 | | |
| 2 | Phototrophic *Haematococcus* extracted biomass plus *Kappaphycus* liquid extract F | 4.7 | a | 9% | 35.2 | a | 13% |
|   | Phototrophic *Haematococcus* extracted biomass plus *Kappaphycus* liquid extract S | 4.6 | a | 5% | 32.8 | a | 32% |
| 3 | Grower Standard Product - Acadian Liquid Seaweed Concentrate F | 4.5 | a | 4% | 35.6 | a | 14% |
|   | Grower Standard Product - Acadian Liquid Seaweed Concentrate S | 5.1 | a | 17% | 32.7 | a | 32% |

Table 8 shows that there was not statistical significance to the results of the *Haematococcus* based composition treatments compared to the UTC regarding whole plant weight.

TABLE 9

Plant Sizing - Root (grams) (A = earlier, B = later)

|   | | Avg. A | | Increase over UTC | Avg. B | | Increase over UTC |
|---|---|---|---|---|---|---|---|
| 1 | UTC - untreated water check F | 0.6 | a | | 3.4 | a | |
|   | UTC - untreated water check S | 0.6 | a | | 3.0 | | |
| 2 | Phototrophic *Haematococcus* extracted biomass plus *Kappaphycus* liquid extract F | 0.7 | a | 18% | 3.7 | a | 6% |
|   | Phototrophic *Haematococcus* extracted biomass plus *Kappaphycus* liquid extract S | 0.7 | a | 10% | 3.4 | a | 13% |
| 3 | Grower Standard Product - Acadian Liquid Seaweed Concentrate F | 0.6 | a | 0% | 4.0 | a | 17% |
|   | Grower Standard Product - Acadian Liquid Seaweed Concentrate S | 0.7 | a | 8% | 3.6 | a | 21% |

Table 9 shows that there was not statistical significance to the results of the *Haematococcus* based composition treatments compared to the UTC regarding root weight.

TABLE 10

Plant Sizing - Shoot (grams) (A = earlier, B = later)

|   | | Avg. A | | Increase over UTC | Avg. B | | Increase over UTC |
|---|---|---|---|---|---|---|---|
| 1 | UTC - untreated water check F | 3.8 | a | | 27.7 | a | |
|   | UTC - untreated water check S | 3.7 | a | | 24.0 | | |
| 2 | Phototrophic *Haematococcus* extracted biomass plus *Kappaphycus* liquid extract F | 4.1 | a | 8% | 31.5 | a | 14% |
|   | Phototrophic *Haematococcus* extracted biomass plus *Kappaphycus* liquid extract S | 3.9 | a | 4% | 29.4 | a | 22% |
| 3 | Grower Standard Product - Acadian Liquid Seaweed Concentrate F | 3.9 | a | 5% | 31.6 | a | 14% |
|   | Grower Standard Product - Acadian Liquid Seaweed Concentrate S | 4.4 | a | 18% | 29.1 | a | 21% |

Table 10 shows that there was not statistical significance to the results of the *Haematococcus* based composition treatments compared to the UTC regarding shoot weight.

TABLE 11

Average Plant Chlorophyll Content (SPAD)

|   |   | A | B | Avg. | Increase over UTC |
|---|---|---|---|---|---|
| 1 | UTC - untreated water check F | 64.7 | — 39.7 a | 52.2 | |
|   | UTC - untreated water check S |   | — 69.7 ab | 69.7 | |
| 2 | Phototrophic *Haematococcus* extracted biomass plus *Kappaphycus* liquid extract F | 65.4 | — 33.4 a | 49.4 | -5% |
|   | Phototrophic *Haematococcus* extracted biomass plus *Kappaphycus* liquid extract S |   | — 74.2 a | 74.2 | 6% |
| 3 | Grower Standard Product - Acadian Liquid Seaweed Concentrate F | 70.6 | — 35.4 a | 53.0 | 2% |
|   | Grower Standard Product - Acadian Liquid Seaweed Concentrate S |   | — 64.5 a | 64.5 | -7% |

Table 11 shows that there was not statistical significance to the results of the *Haematococcus* based composition treatments compared to the UTC regarding chlorophyll content.

TABLE 12

Average Plant Vigor (Visual Scale 0-5)

|   |   | A | B | C | Avg. | Increase over UTC |
|---|---|---|---|---|---|---|
| 1 | UTC - untreated water check F | 3.4 a | 4.5 a | 4.0 a | 4.0 | |
|   | UTC - untreated water check S | 3.5 a | 4.5 a |   | 4.0 | |
| 2 | Phototrophic *Haematococcus* extracted biomass plus *Kappaphycus* liquid extract F | 2.9 a | 4.3 a | 43.7 a | 3.6 | -8% |
|   | Phototrophic *Haematococcus* extracted biomass plus *Kappaphycus* liquid extract S | 3.7 a | 4.0 a |   | 3.9 | -4% |
| 3 | Grower Standard Product - Acadian Liquid Seaweed Concentrate F | 3.2 a | 4.3 a | 4.0 a | 3.8 | -3% |
|   | Grower Standard Product - Acadian Liquid Seaweed Concentrate S | 3.5 a | 4.0 a |   | 3.8 | -6% |

Table 12 shows that there was not statistical significance to the results of the *Haematococcus* based composition treatments compared to the UTC regarding plant vigor, nor was there a numerical advantage.

TABLE 13

Total Unmarketable Plant Weight per Plot (grams)

|   |   | Avg. |   | Increase over UTC |
|---|---|---|---|---|
| 1 | UTC - untreated water check F | 1895.0 | a | |
|   | UTC - untreated water check S | 963.8 | a | |
| 2 | Phototrophic *Haematococcus* extracted biomass plus *Kappaphycus* liquid extract F | 1923.8 | a | 2% |
|   | Phototrophic *Haematococcus* extracted biomass plus *Kappaphycus* liquid extract S | 103.8 | b | -89% |
| 3 | Grower Standard Product - Acadian Liquid Seaweed Concentrate F | 1580.6 | a | -17% |
|   | Grower Standard Product - Acadian Liquid Seaweed Concentrate S | 66.9 | b | -93% |

Table 13 shows that the soil application of the *Haematococcus* based composition had a statistically significant decrease in unmarketable plant weight compared to the UTC, and the foliar application results were not statistically significant compared to the UTC.

TABLE 14

Total Unmarketable Plant Yield per Plot (number)

|   |   | Avg. |   | Increase over UTC |
|---|---|---|---|---|
| 1 | UTC - untreated water check F | 10.8 | a | |
|   | UTC - untreated water check S | 6.0 | a | |
| 2 | Phototrophic *Haematococcus* extracted biomass plus *Kappaphycus* liquid extract F | 11.5 | a | 7% |
|   | Phototrophic *Haematococcus* extracted biomass plus *Kappaphycus* liquid extract S | 1.5 | b | -75% |
| 3 | Grower Standard Product - Acadian Liquid Seaweed Concentrate F | 9.1 | a | -15% |
|   | Grower Standard Product - Acadian Liquid Seaweed Concentrate S | 1.1 | b | -81% |

Table 14 shows that the soil application of the *Haematococcus* based composition had a statistically significant decrease in unmarketable plant yield compared to the UTC, and the foliar application results were not statistically significant compared to the UTC.

TABLE 15

Total Unmarketable Fruit Weight per Plot (grams)

|   |   | Avg. |   | Increase over UTC |
|---|---|------|---|-------------------|
| 1 | UTC - untreated water check F | 178.5 | a | |
|   | UTC - untreated water check S | 56.2 | a | |
| 2 | Phototrophic *Haematococcus* extracted biomass plus *Kappaphycus* liquid extract F | 173.7 | a | −3% |
|   | Phototrophic *Haematococcus* extracted biomass plus *Kappaphycus* liquid extract S | 38.0 | a | −32% |
| 3 | Grower Standard Product - Acadian Liquid Seaweed Concentrate F | 173.2 | a | −3% |
|   | Grower Standard Product - Acadian Liquid Seaweed Concentrate S | 35.3 | a | −37% |

Table 15 shows that the soil and foliar applications of the *Haematococcus* based composition were not statistically significant compared to the UTC for unmarketable fruit weight.

TABLE 16

Total Marketable Plant Weight per Plot (grams)

|   |   | Avg. |   | Increase over UTC |
|---|---|------|---|-------------------|
| 1 | UTC - untreated water check F | 120.6 | a | |
|   | UTC - untreated water check S | 317.5 | c | |
| 2 | Phototrophic *Haematococcus* extracted biomass plus *Kappaphycus* liquid extract F | 281.9 | a | 134% |
|   | Phototrophic *Haematococcus* extracted biomass plus *Kappaphycus* liquid extract S | 1204.4 | a | 279% |
| 3 | Grower Standard Product - Acadian Liquid Seaweed Concentrate F | 502.5 | a | 317% |
|   | Grower Standard Product - Acadian Liquid Seaweed Concentrate S | 1233.1 | a | 288% |

Table 16 shows that the results of the soil application of the *Haematococcus* based composition were statistically significant compared to the UTC for marketable plant weight, and both soil and foliar applications showed large numerical increases of 279% and 134% over the UTC. These results show the small amounts of the *Haematococcus* based composition at a low concentration and low frequency application are effective for not only improving plant weight, put improving plant weight in the higher quality plants (i.e., marketable) when applied to the soil or foliage.

TABLE 17

Total Marketable Plant Yield per Plot (number)

|   |   | Avg. |   | Increase over UTC |
|---|---|------|---|-------------------|
| 1 | UTC - untreated water check F | 0.6 | a | |
|   | UTC - untreated water check S | 2.3 | a | |
| 2 | Phototrophic *Haematococcus* extracted biomass plus *Kappaphycus* liquid extract F | 1.4 | a | 120% |
|   | Phototrophic *Haematococcus* extracted biomass plus *Kappaphycus* liquid extract S | 6.5 | a | 189% |

TABLE 17-continued

Total Marketable Plant Yield per Plot (number)

|   |   | Avg. |   | Increase over UTC |
|---|---|------|---|-------------------|
| 3 | Grower Standard Product - Acadian Liquid Seaweed Concentrate F | 2.8 | a | 340% |
|   | Grower Standard Product - Acadian Liquid Seaweed Concentrate S | 7.1 | a | 217% |

Table 17 shows that the results of the soil and foliar applications of the *Haematococcus* based composition showed large numerical increases of 189% and 120% over the UTC. These results show the small amounts of the *Haematococcus* based composition at a low concentration and low frequency application are effective for not only improving plant yield, put improving plant yield in the higher quality plants (i.e., marketable) when applied to the soil or foliage.

TABLE 18

Total Marketable Fruit Weight per Plot (grams)

|   |   | Avg. |   | Increase over UTC |
|---|---|------|---|-------------------|
| 1 | UTC - untreated water check F | 73.1 | a | |
|   | UTC - untreated water check S | 123.7 | b | |
| 2 | Phototrophic *Haematococcus* extracted biomass plus *Kappaphycus* liquid extract F | 123.9 | a | 69% |
|   | Phototrophic *Haematococcus* extracted biomass plus *Kappaphycus* liquid extract S | 187.1 | a | 51% |
| 3 | Grower Standard Product - Acadian Liquid Seaweed Concentrate F | 115.8 | a | 58% |
|   | Grower Standard Product - Acadian Liquid Seaweed Concentrate S | 66.9 | a | −46% |

Table 18 shows that the results of the soil application of the *Haematococcus* based composition were statistically significant compared to the UTC for marketable fruit weight. The soil application of the *Haematococcus* based composition also showed a numerical increase of 51% over the UTC. The soil application of the *Haematococcus* based composition also outperformed the Acadian product, which showed a 46% decrease compared to the UTC. These results show the small amounts of the *Haematococcus* based composition at a low concentration and low frequency application are effective for not only improving fruit weight, put improving fruit weight in the higher quality plants (i.e., marketable) when applied to the soil.

TABLE 19

Total Production Plant Weight per Plot (grams)

|   |   | Avg. |   | Increase over UTC |
|---|---|------|---|-------------------|
| 1 | UTC - untreated water check F | 2015.6 | a | |
|   | UTC - untreated water check S | 656.3 | c | |
| 2 | Phototrophic *Haematococcus* extracted biomass plus *Kappaphycus* liquid extract F | 2205.6 | a | 9% |
|   | Phototrophic *Haematococcus* extracted biomass plus *Kappaphycus* liquid extract S | 1308.1 | a | 99% |

TABLE 19-continued

Total Production Plant Weight per Plot (grams)

| | Avg. | | Increase over UTC |
|---|---|---|---|
| 3 Grower Standard Product - Acadian Liquid Seaweed Concentrate F | 2083.1 | a | 3% |
| Grower Standard Product - Acadian Liquid Seaweed Concentrate S | 1300.0 | a | 98% |

Table 19 shows that the results of the soil application of the *Haematococcus* based composition were statistically significant compared to the UTC for production plant weight. The soil application of the *Haematococcus* based composition also showed a numerical increase of 99% over the UTC. These results show the small amounts of the *Haematococcus* based composition at a low concentration and low frequency application are effective for not only total production plant weight when applied to the soil.

TABLE 20

Total Production Plant Yield per Plot (number)

| | Avg. | | Increase over UTC |
|---|---|---|---|
| 1 UTC - untreated water check F | 11.4 | a | |
| UTC - untreated water check S | 8.3 | a | |
| 2 Phototrophic *Haematococcus* extracted biomass plus *Kappaphycus* liquid extract F | 12.9 | a | 13% |
| Phototrophic *Haematococcus* extracted biomass plus *Kappaphycus* liquid extract S | 8.0 | a | -3% |
| 3 Grower Standard Product - Acadian Liquid Seaweed Concentrate F | 11.9 | a | 4% |
| Grower Standard Product - Acadian Liquid Seaweed Concentrate S | 8.3 | a | 0% |

Table 20 shows that the results of the soil and foliar applications of the *Haematococcus* based composition were not statistically significant compared to the UTC for production plant yield.

TABLE 21

Average Production Fruit Weight per Plot (grams)

| | Avg. | | Increase over UTC |
|---|---|---|---|
| 1 UTC - untreated water check F | 179.0 | a | |
| UTC - untreated water check S | 80.5 | b | |
| 2 Phototrophic *Haematococcus* extracted biomass plus *Kappaphycus* liquid extract F | 176.3 | a | -2% |
| Phototrophic *Haematococcus* extracted biomass plus *Kappaphycus* liquid extract S | 164.6 | a | 104% |
| 3 Grower Standard Product - Acadian Liquid Seaweed Concentrate F | 174.1 | a | -3% |
| Grower Standard Product - Acadian Liquid Seaweed Concentrate S | 159.8 | a | 98% |

Table 21 shows that the results of the soil application of the *Haematococcus* based composition were statistically significant compared to the UTC for production fruit weight. The soil application of the *Haematococcus* based composition also showed a numerical increase of 104% over the UTC. These results show the small amounts of the *Haematococcus* based composition at a low concentration and low frequency application are effective for not only total production fruit weight when applied to the soil or foliage.

TABLE 22

Utilization (%, ratio of marketable fruit to total fruit produced by weight)

| | Avg. | | Increase over UTC |
|---|---|---|---|
| 1 UTC - untreated water check F | 6.5 | a | |
| UTC - untreated water check S | 45.0 | b | |
| 2 Phototrophic *Haematococcus* extracted biomass plus *Kappaphycus* liquid extract F | 12.0 | a | 85% |
| Phototrophic *Haematococcus* extracted biomass plus *Kappaphycus* liquid extract S | 92.0 | a | 104% |
| 3 Grower Standard Product - Acadian Liquid Seaweed Concentrate F | 18.3 | a | 181% |
| Grower Standard Product - Acadian Liquid Seaweed Concentrate S | 94.6 | a | 110% |

Table 22 shows that the results of the soil application of the *Haematococcus* based composition were statistically significant compared to the UTC for utilization percentage (ratio of marketable fruit to total fruit produced by weight). The soil application of the *Haematococcus* based composition also showed a numerical increase of 104% over the UTC, with the foliar application showing an 85% increase over the UTC. These results show the small amounts of the *Haematococcus* based composition at a low concentration and low frequency application are effective for improving the total quality of the field when applied to the soil or foliage.

Example 4

An experiment was conducted to determine if applications of dried extracted *Haematococcus* biomass to compost for transplanted petunias affected the flowering and growth of petunia plants. Petunias are part of the Solanaceae family. Treatments of dried extracted (i.e., residual) *Haematococcus pluvialis* biomass (RH) that had previously been subjected to drum drying, mechanical lysing, and supercritical carbon dioxide oil extraction processes were tested at an inclusion percentage of 1% and 3% (by volume) and compared to a control. The *Haematococcus pluvialis* was cultured in phototrophic culture conditions, and drum dried before the extraction process. The treatments consisted of mixing the volume of dried microalgae with soil mix comprised of 80% peat moss, 20% West+MPC compost mix. The treatments were applied to 19 week old *petunia* plant plugs in two liter pots.

Each treatment was applied in three replicates, with the average of the three replicates being used to compare the experimental data. Treatments were laid out in a randomized block design in a heated greenhouse on benches. Quality scores were assigned on four assessment dates (based on visual observations of the plants) at 5, 7, 8, and 11 weeks after application of the treatments. The results are shown below in Table 23.

TABLE 23

Average Quality Score

| Treatments | Assessment Date | | | |
|---|---|---|---|---|
| | 5 weeks | 7 weeks | 9 weeks | 11 weeks |
| Control (untreated) | 7.22 | 7.33 | 7.00 | 6.78 |
| 3% RH | 7.33 | 6.67 | 7.00 | 6.89 |
| 1% RH | 7.44 | 7.00 | 6.78 | 6.67 |

As shown in Table 23, RH at 3% ended with a quality score higher than the control.

Example 5

An experiment was conducted to determine if applications of dried extracted *Haematococcus* biomass to the soil affected the germination and vigor of *cannabis* plants. Three seeds were planted in each six inch diameter pot. The pots were filled with 50% Promix, 25% sterilized Maury silt loam soil, and 25% sand. All plants were managed under controlled greenhouse conditions with 18 hour per day light. The treatments were applied once every two weeks starting at the time of seeding and compared to an untreated control. All plants received normal nitrogen fertilization. Treatments of dried extracted (i.e., residual) *Haematococcus pluvialis* biomass that had previously been subjected to drum drying, mechanical lysing, and supercritical carbon dioxide oil extraction processes were tested at an inclusion percentage of 1%, 3%, and 5% (by volume) of the soil. Statistical analysis of the germination results at 2 and 3 days after seeding are shown in Tables 24 and 25. Statistical analysis of the seedling vigor results at 4 and 7 days after seeding are shown in Tables 26 and 27. Statistical analysis of the seedling dry weight is shown in Table 28.

TABLE 24

% Germination 2 Days After Seeding

| Treatment | Statistical Group Identifier | Least Square Mean |
|---|---|---|
| Untreated Control | AB | 31 |
| Ext. Haem. 1% | ABC | 22 |
| Ext. Haem. 3% | BC | 6 |
| Ext. Haem. 5% | C | 0 |

TABLE 25

% Germination 3 Days After Seeding

| Treatment | Statistical Group Identifier | Least Square Mean |
|---|---|---|
| Ext. Haem. 1% | AB | 85 |
| Untreated Control | AB | 78 |
| Ext. Haem. 3% | AB | 76 |
| Ext. Haem. 5% | B | 49 |

TABLE 26

Seedling Vigor 4 Days After Seeding

| Treatment | Statistical Group Identifier | Least Square Mean |
|---|---|---|
| Untreated Control | A | 7.00 |
| Ext. Haem. 1% | A | 6.75 |

TABLE 26-continued

Seedling Vigor 4 Days After Seeding

| Treatment | Statistical Group Identifier | Least Square Mean |
|---|---|---|
| Ext. Haem. 3% | A | 6.25 |
| Ext. Haem. 5% | B | 3.75 |

TABLE 27

Seedling Vigor 7 Days After Seeding

| Treatment | Statistical Group Identifier | Least Square Mean |
|---|---|---|
| Ext. Haem. 1% | A | 6.50 |
| Untreated Control | A | 6.25 |
| Ext. Haem. 3% | AB | 5.75 |
| Ext. Haem. 5% | B | 4.00 |

TABLE 28

Seddling Dry Weight Days After Seeding

| Treatment | Statistical Group Identifier | Least Square Mean |
|---|---|---|
| Ext. Haem. 1% | A | 0.8320 |
| Untreated Control | A | 0.78375 |
| Ext. Haem. 3% | AB | 0.6835 |
| Ext. Haem. 5% | B | 0.4925 |

As shown in the Tables 25, 27, and 28, the 1% treatment showed a numerical advantage over the untreated control.

Example 6

An experiment was conducted to determine if applications of dried extracted *Haematococcus* biomass to the soil affected the yield of kidney beans. Kidney beans are part of the Fabaceae family. Treatments of dried extracted (i.e., residual) *Haematococcus pluvialis* biomass that had previously been subjected to drum drying, mechanical lysing, and supercritical carbon dioxide oil extraction processes were tested and compared to a control. The tested dried extracted *Haematococcus* treatments consisted of the application of 92 grams/acre, 184 grams/acre, and 368 grams/acre during in-furrow planting and six broadcast applications at 14 day intervals.

A randomized block design was set up in two fields, one located in Lafayette, Ind. and one located in Brookings, S. Dak. An early kidney bean variety was seeded into plots and all treatments, including the control, received standard Nitrogen-Phosphours-Potassium (NPK) treatments. Planting times were delayed to the very end of the optimal seeding window due to excessively wet weather. Stand establishment for the fields was reported as difficult, and the stand uniformity was reported as acceptable but not ideal. Emergence and vegetative biomass at the end of growth phase and bean yield during harvest were quantified. Mid-season and at-harvest soil fertility was profiled by Motzz Laboratories (Phoenix, Ariz.). Soil fertility analysis revealed that the South Dakota site had, on average, twice the amount of organic matter, CEC and multiple important micronutrients, including calcium, magnesium, nickel and boron compared to the Indiana location Results for the South Dakota location are shown in Table 29, and the results for the Indiana location are shown in Table 30.

TABLE 29

| Treatment | Stand 14 Days After Planting | Vigor 14 Days After Planting | Stand 28 Days After Planting | Vigor 28 Days After Planting | Fresh Wt avg (g) | Dry Wt avg (g) | Dry: Fresh Ratio | Adj. Bu. Yield 13% | Seeds/ lb | Pods/ Plant | Moist % |
|---|---|---|---|---|---|---|---|---|---|---|---|
| Untreated Control | 76.4 | 2.6 | 74.3 | 2.9 | 158.7 | 17.8 | 0.11 | 35.8 | 704 | 21.4 | 13.2 |
| Ext. Haem. 92 g/acre | 82.1 | 2.3 | 76.4 | 2.6 | 154.9 | 17.0 | 0.11 | 35.3 | 715 | 20.2 | 12.8 |
| Ext. Haem. 184 g/acre | 80.4 | 2.5 | 84.6 | 2.6 | 159.3 | 19.3 | 0.12 | 36.5 | 684 | 21.2 | 12.9 |
| Ext. Haem. 368 g/acre | 85.7 | 2.5 | 78.2 | 2.8 | 145.5 | 16.7 | 0.12 | 37.0 | 695 | 19.8 | 13.0 |
| Prob > F | 0.75 | 0.52 | 0.27 | 0.55 | 0.80 | 0.49 | 0.65 | 0.99 | 0.76 | 0.79 | 0.53 |
| CV | 12 | 21 | 11 | 25 | 21 | 31 | 19 | 15 | 5 | 8 | 4 |

As shown in Table 29, the treated plots had a higher numerical stand rating 14 and 28 days after planting than the untreated control. The 92 g/acre treatment showed a numerical advantage over the untreated control for seeds per pound. The 184 g/acre treatment showed a numerical advantage over the untreated control for average fresh weight, average dry weight, dry:fresh weight ratio, and adjusted bushel yield. The 368 g/acre treatment showed a numerical advantage over the untreated control for dry:fresh weight ratio, and adjusted bushel yield.

TABLE 30

| Treatment | Stand 14 Days After Planting | Vigor 14 Days After Planting | Stand 28 Days After Planting | Vigor 28 Days After Planting | Fresh Wt avg (g) | Dry Wt avg (g) | Dry: Fresh Ratio | Adj. Bu. Yield 13% | Seeds/ lb | Pods/ Plant | Moist % |
|---|---|---|---|---|---|---|---|---|---|---|---|
| Untreated Control | 85.0 | 4.25 | 3.4 | 85.3 | 4.25 | 3.4 | 17.91 | 3.61 | 0.21 | 45.0 | 37.0 |
| Ext. Haem. 92 g/acre | 79.9 | 4.50 | 3.6 | 80.0 | 4.50 | 3.6 | 14.90 | 3.10 | 0.22 | 42.6 | 34.5 |
| Ext. Haem. 184 g/acre | 92.8 | 4.13 | 3.4 | 93.1 | 4.13 | 3.4 | 16.00 | 3.23 | 0.21 | 39.5 | 32.5 |
| Ext. Haem. 368 g/acre | 86.5 | 4.13 | 3.4 | 87.3 | 4.13 | 3.4 | 20.57 | 4.10 | 0.21 | 33.7 | 27.7 |
| Prob > F | 0.65 | 0.79 | 0.89 | 0.64 | 0.79 | 0.89 | 0.84 | 0.82 | 0.37 | 0.030 | 0.013 |
| CV | 18 | 13 | 17 | 18 | 13 | 17 | 42 | 35 | 8 | 22.16 | 21 |

As shown in Table 30, the 184 and 368 g/acre treated plots had a higher numerical stand rating 14 and 28 days after planting than the untreated control. The 92 g/acre treatment showed a numerical advantage over the untreated control for average fresh weight and average dry weight. The 368 g/acre treatment showed a numerical advantage over the untreated control for dry:fresh weight ratio and adjusted bushel yield.

Example 7—Fabaceae (Leguminosae)

Experiments are conducted to test effects of application of an extracted *Haematococcus* based composition to crop plants of the family Fabaceae (Leguminosae). Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 8—Poaceae

Experiments are conducted to test effects of application of an extracted *Haematococcus* based composition to crop plants of the family Poaceae. Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 9—Roasaceae

Experiments are conducted to test effects of application of an extracted *Haematococcus* based composition to crop plants of the family Roasaceae. Application is done as in other examples herein, such that, in various treatments, (a) seeds are wetted or soaked in the composition; ((b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 10—Vitaceae

Experiments are conducted to test effects of application of an extracted *Haematococcus* based composition to crop plants of the family Vitaceae. Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 11—Brassicaeae (Cruciferae)

Experiments are conducted to test effects of application of an extracted *Haematococcus* based composition to crop plants of the family Brassicaeae (Cruciferae). Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 12—Caricaceae

Experiments are conducted to test effects of application of an extracted *Haematococcus* based composition to crop plants of the family Caricaceae. Application is done as in other examples herein, such that, in various treatments, (a) seeds are wetted or soaked in the composition; ((b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 13—Malvaceae

Experiments are conducted to test effects of application of an extracted *Haematococcus* based composition to crop plants of the family Malvaceae. Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 14—Sapindaceae

Experiments are conducted to test effects of application of an extracted *Haematococcus* based composition to crop plants of the family Sapindaceae. Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 15—Anacardiaceae

Experiments are conducted to test effects of application of an extracted *Haematococcus* based composition to crop plants of the family Anacardiaceae. Application is done as in other examples herein, such that, in various treatments, (a) seeds are wetted or soaked in the composition; (b) seeds are coated in the composition; (c) the composition is mixed with a solid growth medium before planting the seeds; (d) the composition is applied to soil pre-germination; (e) the composition is applied to soil post-germination; (f) the composition is applied periodically to soil during the growing season; and/or (g) the composition is applied to leaves of the plants once or periodically during the growing season. Results are measures for appropriate plant characteristics including: seed germination rate, seed germination time, seedling emergence, seedling emergence time, seedling size, plan fresh weight, plant dry weight, utilization, fruit production, leaf production, leaf formation, leaf size, leaf area index, plant height, thatch height, plant health, plant resistance to salt stress, plant resistance to heat stress, plant resistance to heavy metal stress, plant resistance to drought, maturation time, yield, root length, root mass, color, insect damage, blossom end rot, softness, plant quality, fruit quality, flowering, and sun burn. Results show at least a 10% quantitative improvement and/or a statistically significant improvement as to at least one characteristic under at least one mode of application (a-g) of the composition.

Example 16

An experiment was performed to determine the effect of treating *Arabidopsis thaliana* with extracted *Haematococcus pluvialis* biomass under normal growth conditions and under salt stressed conditions. The bioassay was initiated using four day old plantlets grown on half strength Murashige and Skoog (MS) medium, supplement with 1% (w/v) sucrose and solidified with 0.4% (w/v) Phytagel in square petri plates. Each plate contained five replicate plantlets. Plantlets were transferred on medium supplemented with concentrations of 0.1%, 0.01%, or 0.001% of extracted *Haematococcus pluvialis* biomass and compared to an untreated control. The salt stressed plantlets were also supplemented with 100 mM of NaCl. Seven days after the plantlets were treated plant dry weight, root length, amount of chlorotic leaves, and the amount of plants with chlorosis were measured. The results are shown in Tables 31-33, which display the results for each tested concentration with respect to the untreated control.

TABLE 31

Growth (No Salt Stress)

| Concentration | Dry Weight % Difference vs. Control | Root Length % Difference vs. Control |
| --- | --- | --- |
| 0.1% | −3.6 | −82.9 |
| 0.01% | +50.9 | +1.9 |
| 0.001% | +27.3 | +9.6 |

TABLE 32

Salt Stress

| Concentration | Dry Weight % Difference vs. Control | Root Length % Difference vs. Control |
| --- | --- | --- |
| 0.1% | +8.8 | −96.4 |
| 0.01% | −2.9 | +2.8 |
| 0.001% | −20.6 | +26.7 |

TABLE 33

Chlorosis

| Concentration | Chlorotic leaves % Difference vs. Control | Plants with Chlorosis % Difference vs. Control |
| --- | --- | --- |
| 0.1% | −58.8 | −37.1 |
| 0.01% | −10.6 | +15.3 |
| 0.001% | +34.7 | +57.2 |

As shown in Table 31, the 0.01% treatment showed the largest improvement in plant dry weight over the control in normal growth conditions, with the 0.001% treatment also showing an improvement over the control. The 0.001% treatment showed the largest improvement in root length over the control, with the 0.01% treatment also showing an improvement over the control. As shown in Table 32, the 0.1% treatment showed an improvement in plant dry weight over the control in salt stress conditions. The 0.001% showed the largest improvement in root length over the control, with the 0.01% treatment also showing an improvement over the control. As shown in Table 33, the 0.1% treatment had the largest reduction in chlorotic leaves and plants with chlorosis compared to the control, and the 0.01% also showed a reduction in Chlorotic leaves compared to the control.

Example 17

An experiment was performed to determine the effect of treating *Arabidopsis thaliana* with extracted *Haematococcus pluvialis* biomass under normal growth conditions and under salt stressed conditions. The bioassay was initiated using two week old *Arabidopsis* plants grown on Jiffy pellets (peat moss pellets). Five replicates of each plant were performed for the treatments. Plants on Jiffy pellets were placed on trays with concentrations of 0.1%, 0.01%, or 0.001% of extracted *Haematococcus pluvialis* biomass at 40 mL/plant and compared to an untreated control. The salt stressed plantlets were also supplemented with 200 mM of NaCl. Five days after the first treatment the *Haematococcus* biomass treatment was repeated, but additional salt was not added. Ten days after the first treatment the plant dry weight was measured. The results are shown in Tables 34-35, which display the results for each tested concentration with respect to the untreated control.

TABLE 34

Growth (No Salt Stress)

| Concentration | Dry Weight % Difference vs. Control |
|---|---|
| 0.1% | −17.9 |
| 0.01% | +13.1 |
| 0.001% | +35.9 |

TABLE 35

Salt Stress

| Concentration | Dry Weight % Difference vs. Control |
|---|---|
| 0.1% | −18.3 |
| 0.01% | +27.3 |
| 0.001% | +30.5 |

As shown in Tables 34 and 35, the 0.001% treatment showed the largest improvement in plant dry weight over the control in normal growth and salt stress conditions, with the 0.01% treatment also showing an improvement over the control.

Example 18

An experiment was performed to determine the effect of treating *Arabidopsis thaliana* with extracted *Haematococcus pluvialis* biomass under normal growth conditions and under temperature stressed conditions. The bioassay was initiated using four day old plantlets grown on half strength Murashige and Skoog (MS) medium, supplement with 1% (w/v) sucrose and solidified with 0.7% (w/v) agar in square petri plates. Each plate contained five replicate plantlets. Plantlets were transferred on medium supplemented with concentrations of 0.01% or 0.001% of extracted *Haematococcus pluvialis* biomass and compared to an untreated control. After seven days, half of the plates were placed in a growth chamber and subjected to three days of continuous temperature stress (35° C.) while the other half were maintained at about 22° C. Following the temperature stress period, the plantlets were allowed to grow for seven additional days, and plant dry weight was measured at the end. The results are shown in Tables 36-37, which display the results for each tested concentration with respect to the untreated control.

TABLE 36

Growth (No temperature Stress)

| Concentration | Dry Weight % Difference vs. Control |
|---|---|
| 0.01% | +36.9 |
| 0.001% | +19.2 |

TABLE 37

Temperature Stress

| Concentration | Dry Weight % Difference vs. Control |
|---|---|
| 0.01% | −0.7 |
| 0.001% | +54.8 |

As shown in Tables 36, the 0.01% treatment showed the largest improvement in plant dry weight over the control in normal growth conditions, with the 0.001% treatment also showing an improvement over the control. As shown in Tables 37, the 0.001% treatment showed an improvement in plant dry weight over the control in temperature stressed conditions.

Example 19

An experiment was performed to determine the effect of treating *Phaseolus aureus* (mung bean) with extracted *Haematococcus pluvialis* biomass under normal growth conditions. The biomass as initiated using cut mung bean seedlings which were grown in vials supplemented with concentrations of 0.1%, 0.01%, or 0.001% of extracted *Haematococcus pluvialis* biomass and compared to an untreated control. The root growth parameters of distance of root growth from meristem, number of roots, and root length were measured. The results are shown in Table 38, which display the results for each tested concentration with respect to the untreated control.

TABLE 38

| Concentration | Distance of Root Growth from Meristem % Difference vs. Control | Number of Roots % Difference vs. Control | Root Length % Difference vs. Control |
|---|---|---|---|
| 0.1% | +7.7 | +32.0 | +35.6 |
| 0.01% | −15.4 | +26.0 | +15.6 |
| 0.001% | −23.1 | +22.0 | +88.9 |

As shown in Table 38, the 0.1% treatment showed an improvement in plant dry weight over the control. All treatments showed an improvement in number of roots over the control, with the 0.1% treatment showing the largest improvement. All treatments showed an improvement in root length over the control, with the 0.001% treatment showing the largest improvement.

Example 20

An experiment was performed to determine the effect of treating *Arabidopsis thaliana* with extracted *Haematococcus pluvialis* biomass under conditions where the plants are exposed to *Sclerotinia sclerotiorum*. The bioassay was initiated using four week old plantlets grown on Jiffy pellets (peat moss pellets). Plants on Jiffy pellets were placed on trays and sprayed with concentrations of 0.1% or 0.01% of extracted *Haematococcus pluvialis* biomass and compared to an untreated control. The day after the application of the treatments, the plugs of *Scelerotinia sclerotiorum* were placed on two leaves per plant. The disease severity (diameter of infected area around a plug) was recorded for days 2, 3, 4, and 5. The results are shown in Table 39, which display the results for each tested concentration with respect to the untreated control.

TABLE 39

| Concentration | Diameter of disease infected area % Difference vs. Control |
|---|---|
| 0.1% | −3.6 |
| 0.01% | +62.6 |

As shown in Tables 39, the 0.01% treatment showed a reduced diameter of the infected area on the plants over the control.

ASPECTS OF THE INVENTION

In one non-limiting embodiment, a method for enhancing emergence of a plant from seed may include: administering a liquid composition comprising *Haematococcus* cells in which the cells consist essentially of cells that have been subjected to drying, mechanical lysing, and extraction processes, in a concentration in the range of 0.003-0.080% solids by weight to a planted seed in an amount effective to enhance emergence of seeds in a population of such seeds compared to seeds in a substantially identical population of untreated seeds.

In some embodiments, the administration may include contacting the soil in the immediate vicinity of the planted seed with an effective amount of the liquid composition. In some embodiments, the liquid composition may comprise 0.004-0.080% solids by weight of *Haematococcus* cells. In some embodiments, the liquid composition may be administered at a rate in the range of 50-150 gallons per acre.

In some embodiments, the liquid composition may be pasteurized. In some embodiments, the liquid composition may further comprise stabilizing means suitable for plants. In some embodiments, the liquid composition may further comprise whole *Chlorella* cells cultured in mixotrophic conditions. In some embodiments, the *Chlorella* cells may be cultured in non-axenic mixotrophic conditions. In some embodiments, the liquid composition may further comprise a liquid extract from *Kappaphycus*.

In some embodiments, the number of plants emerged from the soil may be increased by at least 30% compared to a substantially identical population of untreated seeds of plants.

In another non-limiting embodiment, a method of enhancing emergence of a plant from seed may comprise: Providing a liquid composition comprising a *Haematococcus* cells in which the cells consist essentially of cells that have been subjected to drying, mechanical lysing, and extraction processes, in a concentration in the range of 5-30% solids by weight; Diluting the liquid composition with water to a concentration in the range of 0.003-0.080% solids by weight of *Haematococcus* cells; and Administering the liquid composition to a planted seed in an amount effective to enhance emergence of seeds in a population of such seeds compared to seeds in a substantially identical population of untreated seeds.

In another non-limiting embodiment, a method for enhancing yield of a plant may comprise: administering a liquid composition comprising *Haematococcus* cells in which the cells consist essentially of cells that have been subjected to drying, mechanical lysing, and extraction processes, in a concentration in the range of 0.001-0.400% solids by weight to a plant in an amount effective to increase utilization in a population of such plants compared to a substantially identical population of untreated plants.

In some embodiments, the administration may comprise contacting foliage of the plants with an effective amount of the liquid composition. In some embodiments, the liquid composition may comprise a concentration in the range of 0.003-0.080% solids by weight of the *Haematococcus* cells. In some embodiments, the liquid composition may be administered at a rate in the range of 10-50 gallons/acre. In some embodiments, the liquid composition may be administered by spraying. In some embodiments, the liquid composition may be administered every 3-28 days. In some embodiments, the liquid composition may be administered every 4-10 days. In some embodiments, the liquid composition may be first administered 5-14 days after the plant emerges from the soil.

In some embodiments, the liquid composition may comprise a concentration in the range of 0.003-0.055% by weight of *Haematococcus* cells. In some embodiments, the liquid composition may comprise a concentration in the range of 0.040-0.360% solids by weight of *Haematococcus* cells. In some embodiments, the liquid composition may be administered to the soil by a soil drench application.

In some embodiments, the method may further comprise increasing at least one form the group consisting of marketable plant weight, marketable plant yield, and marketable fruit weight. In some embodiments, the utilization may be increased by at least 80% compared to a substantially identical population of untreated plants. In some embodiments, the marketable plant weight may be increased by at least 125% compared to a substantially identical population of untreated plants. In some embodiments, the marketable plant yield may be increased by at least 100% compared to a substantially identical population of untreated plants. In some embodiments, the marketable fruit weight may be increased by at least 50% compared to a substantially identical population of untreated plants.

In another non-limiting embodiment, a method of enhancing yield of a plant may comprise: Providing a liquid composition comprising *Haematococcus* cells in which the cells consist essentially of cells that have been subjected to drying, mechanical lysing, and extraction processes in a concentration in the range of 5-30% solids by weight; Diluting the liquid composition with water to a concentration in the range of 0.001-0.400% solids by weight of *Haematococcus* cells; and Administering the liquid composition to a plant in an amount effective to increase plant yield in a population of such plants compared to a substantially identical population of untreated plants.

In another non-limiting embodiment, a composition may comprise: *Haematococcus* cells in which the cells consist essentially of cells that have been subjected to drying, mechanical lysing, and extraction processes in a concentration in the range of 0.003-0.080% solids by weight, and water. In some embodiments, the composition may further comprise whole *Chlorella* cells cultured in mixotrophic conditions. In some embodiments, the composition may further comprise a liquid extract from *Kappaphycus*.

In another non-limiting embodiment, a composition may comprise: *Haematococcus* cells in which the cells consist essentially of cells that have been subjected to drying, mechanical lysing, and extraction processes in a concentration in the range of 5-30% solids by weight, and water.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). All provided ranges of values are intended to include the end points of the ranges, as well as values between the end points.

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims and/or aspects appended hereto as permitted by applicable law.

What is claimed is:

1. A method of plant enhancement comprising administering to a plant, seedling, or seed a composition comprising 0.1-20% by volume of *Haematococcus* cells in which the cells consist essentially of cells that have been subjected to drying, mechanical lysing, and extraction processes to enhance at least one plant characteristic selected from the group consisting of: seed germination rate, seed germination time, seedling emergence, seedling emergence time, and utilization,
    wherein the method further comprises administering to the plant, seedling, or seed an extract of *Kappaphycus*; utilization is measured as a ratio of marketable plants or fruit to unmarketable plants or fruit; and the plant, seedling or seed is from the Solanaceae plant family.

2. The method of claim 1, wherein the concentration of *Haematococcus* cells is 1-5% by volume.

3. The method of claim 1, wherein the *Haematococcus* cells are dried by at least one method selected from the group consisting of: freeze drying, spray drying, drum drying, crossflow air drying, solar drying, thin film convection oven drying, vacuum shelf drying, pulse combustion drying, flash drying, furnace drying, belt conveyor drying, and refractance window drying.

4. The method of claim 1, wherein the administering is selected from: coating a seed with the composition prior to planting; administering the composition to a solid growth medium prior to or after the planting of a seed, seedling, or plant; and mixing the composition in a suitable solid growth medium prior to planting a seed, seedling, or plant.

5. The method of claim 4, wherein the solid growth medium comprises at least one from the group consisting of: soil, potting mix, compost, or inert hydroponic material.

6. The method of claim 1, wherein the composition is administered at a rate of 50-500 grams of *Haematococcus* cells per acre.

7. The method of claim 6, wherein the administering is selected from: in-furrow application during planting, and broadcast application.

8. The method of claim 1, wherein a liquid extract of *Kappaphycus* is administered.

9. The method of claim 1, further comprising administering *Chlorella* cells to the plant, seedling, or seed.

10. The method of claim 9, wherein the *Chlorella* cells are cultured in mixotrophic conditions.

11. The method of claim 9, wherein the *Chlorella* cells are whole cells.

12. The method of claim 9, wherein the *Chlorella* cells are lysed.

13. The method of claim 1, wherein the composition is administered to soil by a low volume irrigation system or a soil drench application.

14. The method of claim 1, wherein the composition is administered to foliage of the plant.

15. The method of claim 1, wherein the enhanced seed germination rate, seed germination time, seedling emergence, and/or seedling emergence time results in accelerated achievement of the hypocotyl stage, accelerated protrusion of a stem from the soil, accelerated achievement of the cotyledon stage, and/or accelerated leaf formation.

16. The method of claim 1, wherein the enhanced utilization results in increased marketable plant weight, increased marketable plant yield, increased marketable fruit weight, and/or increased ratio of marketable fruit to unmarketable fruit.

\* \* \* \* \*